(12) United States Patent
Gondal et al.

(10) Patent No.: US 10,131,602 B1
(45) Date of Patent: *Nov. 20, 2018

(54) CATALYTIC METHANOL FORMATION FROM CARBON DIOXIDE WITH A TEMPLATED INDIUM CATALYST

(71) Applicant: KING FAHD UNIVERSITY OF PETROLEUM AND MINERALS, Dhahran (SA)

(72) Inventors: Muhammad Ashraf Gondal, Dhahran (SA); Mohamed A. Dastageer, Dhahran (SA); Umair Baig, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/034,612

(22) Filed: Jul. 13, 2018

Related U.S. Application Data

(63) Continuation of application No. 15/807,134, filed on Nov. 8, 2017, now Pat. No. 10,047,027.

(51) Int. Cl.
| | |
|---|---|
| *C07C 29/00* | (2006.01) |
| *C07C 31/04* | (2006.01) |
| *B01J 23/00* | (2006.01) |
| *B01J 37/00* | (2006.01) |
| *C07C 29/153* | (2006.01) |
| *B01J 37/34* | (2006.01) |
| *C01B 32/50* | (2017.01) |
| *B01J 23/08* | (2006.01) |
| *G01N 23/20* | (2018.01) |
| *C25B 1/04* | (2006.01) |
| *G01N 30/02* | (2006.01) |

(52) U.S. Cl.
CPC ............. *C07C 29/153* (2013.01); *B01J 23/08* (2013.01); *B01J 37/345* (2013.01); *C01B 32/50* (2017.08); *C07C 31/04* (2013.01); *C25B 1/04* (2013.01); *G01N 23/20075* (2013.01); *G01N 2030/025* (2013.01)

(58) Field of Classification Search
CPC ........ C07C 29/153; C07C 31/04; B01J 23/08; B01J 37/345
See application file for complete search history.

(56) References Cited

U.S. PATENT DOCUMENTS

2015/0321174 A1  11/2015  Ozin et al.

FOREIGN PATENT DOCUMENTS

| CN | 102978655 A | 3/2013 |
| TW | I317301 B | 11/2009 |
| TW | I361722 B | 4/2012 |

OTHER PUBLICATIONS

A.H. Yahaya, et al., "Selective laser enhanced photocatalytic conversion of $CO_2$ into methanol", Chemical Physics Letters, vol. 400, Issues 1-3, Dec. 11, 2004, pp. 206-212.

M. A. Gondal. et al., "Enhanced photo-catalytic activity of ordered mesoporous indium oxide nanocrystals in the conversion of $CO_2$ into methanol". Journal of Environmental Science and Health, Part A, > Toxic/Hazardous Substances and Environmental Engineering, Apr. 3, 2017, pp. 1-9 (Abstract only).

Der-Shing Lee, et al., "Photocatalytic reduction of carbon dioxide with water on $InVO_4$ with NiO cocatalysts", Journal of CO2 Utilization, vol. 10, Jun. 2015, pp. 1-6 (Abstract only).

Muhammad Tahir, et al., "Selective photocatalytic reduction of $CO_2$ by $H_2O/H_2$ to $CH_4$ and $CH_3OH$ over Cu-promoted $In_2O_3/TiO_2$ nanocatalyst", Applied Surface Science, vol. 389, Dec. 15, 2016, pp. 46-55.

Mohammed A. Gondal, et al., "Pulsed laser-induced photocatalytic reduction of greenhouse gas $CO_2$ into methanol: A value-added hydrocarbon product over SiC", Journal of Environmental Science and Health, Part A. vol. 47, No. 11, 2012, pp. 1571-1576.

Jotheeswari Kothandaraman. et al., "Conversion of $CO_2$ from Air into Methanol Using a Polyamine and a Homogeneous Ruthenium Catalyst", J. Am. Chem. Soc., vol. 138, No. 3, 2016, pp. 778-781.

Atul Bansode, et al., "Towards Full One-Pass Conversion of Carbon Dioxide to Methanol and Methanol-Derived Products". Journal of Catalysis, vol. 309, 2014, pp. 66-70 (Abstract only).

*Primary Examiner* — Sikarl A Witherspoon
(74) *Attorney, Agent, or Firm* — Oblon, McClelland, Maier & Neustadt, L.L.P.

(57) ABSTRACT

A method of forming methanol by irradiating a mixture comprising water, carbon dioxide, and a photocatalyst with UV light to photo-catalytically reduce the carbon dioxide thereby forming methanol, wherein the photocatalyst comprises non-templated indium-oxide nanoparticles and/or templated indium-oxide nanoparticles. Various combinations of the embodiments of the templated indium-oxide nanoparticles and the non-templated indium-oxide nanoparticles photocatalyst as well as the method of forming methanol are provided.

9 Claims, 16 Drawing Sheets

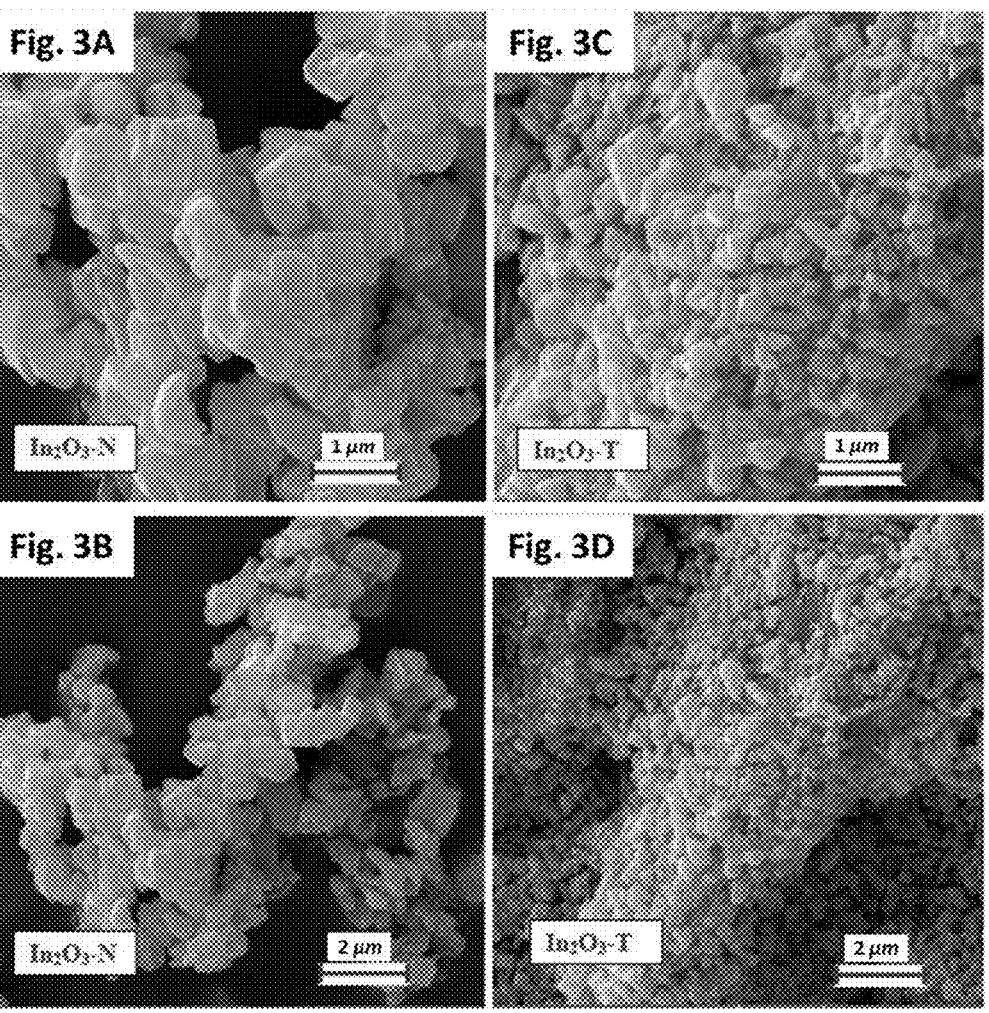

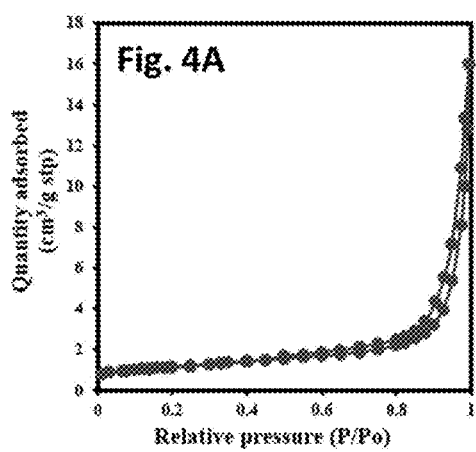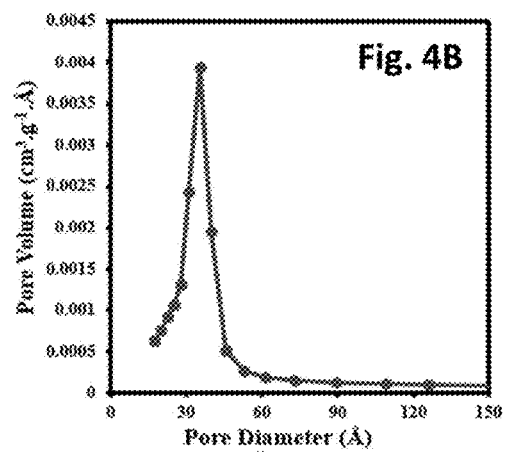

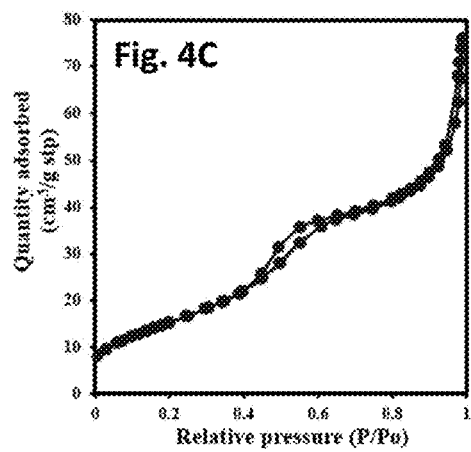
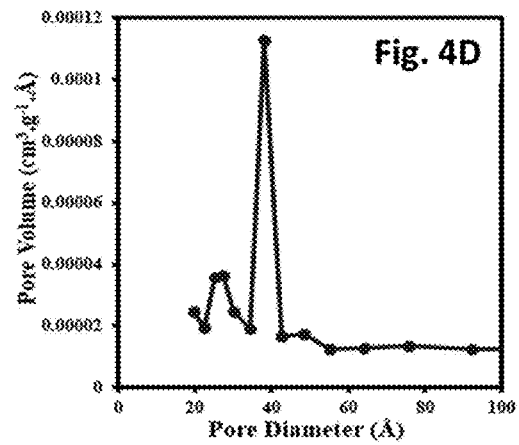

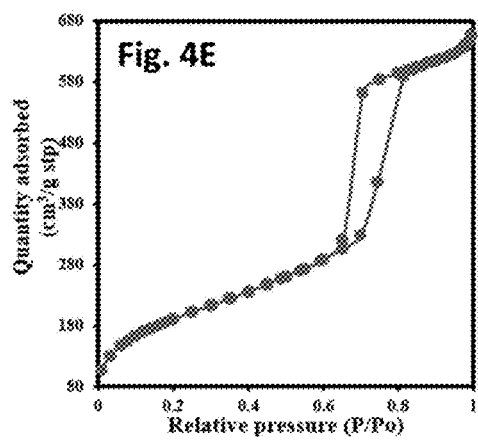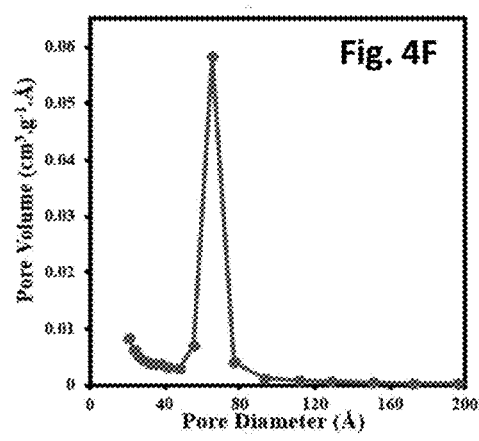

US 10,131,602 B1

CATALYTIC METHANOL FORMATION FROM CARBON DIOXIDE WITH A TEMPLATED INDIUM CATALYST

CROSS-REFERENCE TO RELATED APPLICATIONS

The present application is a Continuation of Ser. No. 15/807,134, now allowed, having a filing date of Nov. 8, 2017.

STATEMENT OF FUNDING ACKNOWLEDGEMENT

The funding support provided by the King Abdul Aziz City for Science and Technology (KACST) through TIC-KFUPM project number CCS-16 under KACST-Technology Center on Carbon Capture and Sequestration at KFUPM, is gratefully acknowledged.

STATEMENT REGARDING PRIOR DISCLOSURES BY THE INVENTOR OR A JOINT INVENTOR

Gondal et al., *Enhanced photo-catalytic activity of ordered mesoporous indium-oxide nanocrystals in the conversion of $CO_2$ into methanol*. Journal of Environmental Science and Health, Part A, Volume 52, Issue 8, Apr. 3, 2017, Pages 785-793, which is incorporated by reference in its entirety.

BACKGROUND OF THE INVENTION

Technical Field

The present invention relates to a method of forming methanol by photo-catalytically reducing carbon dioxide in the presence of a photocatalyst that comprises templated indium-oxide nanoparticles and/or non-templated indium-oxide nanoparticles.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The excessive use of fossil fuels, vast industrialization, and human activities in the past few years have tremendously increased the amount of $CO_2$ in the atmosphere. Several strategies have been put forward to regulate anthropogenic emission of $CO_2$. These strategies range from human behavioral changes to technological innovations such as efficient energy conversion and carbon capture and sequestration (CCS) to partially mitigate $CO_2$ emissions. Currently, one major hurdle to use large scale CCS plants, particularly in power plants, is the cost of the carbon capture process. Accordingly, using a CCS plant to capture carbon dioxide approximately increases the total cost of producing one megawatt power by at least 25%, due to the extra costs of capturing, compressing, and storing carbon dioxide [W. N. Wang, *Aerosol Air Qual Res.* 14, 533 (2014)]. In order to make $CO_2$ conversion commercially more acceptable, it is quite imperative to establish methodologies to convert $CO_2$ into low carbon fuels such as methanol, methane, carbon monoxide, and formic acid.

In recent years, various approaches have been reported for converting $CO_2$ into value added hydrocarbons. Among those, thermochemical [W. C. Chueh, S. M. Haile, *ChemSusChem.* 2, 735 (2009)], electrochemical [T. Abe, T. Yoshida, S. Tokita, F. Taguchi, H. Imaya, M. Kaneko, *J. Electroanal. Chem.* 412, 125 (1996); M. Jitaru, D. A. Lowy, M. Toma, B. C. Toma, L. Oniciu, *J. Appl. Elecrochem.* 27, 875 (1997)], photocatalytic [T. Inoue, A. Fujishima, S. Konishi, K. Honda, *Nature.* 277, 637 (1979)], and biological [R. E. Blankenship, D. M. Tiede, J. Barber, *Science.* 332, 805 (2011)] methods are widely investigated. Since $CO_2$ is very stable and inert, a significant amount of energy is required to convert $CO_2$ into value added hydrocarbons. However, photocatalytic conversion of $CO_2$ has become one of the most popular methods, due to the fact that it is simple, less cumbersome, and above all has the prospect of harnessing solar energy, which is cheap, clean, ecologically safe, and inexhaustible. For photocatalytic conversion of $CO_2$ into value added hydrocarbons, semiconducting materials are generally used as the photocatalyst to absorb photons having sufficient energy to generate electron-hole pairs that mediate photo-oxidation and photo-reduction reactions [M. A. Gondal, M. A. Dastageer, S. G. Rashid, S. MZubair, M. A. Ali, D. H. Anjum J. H. Lienhard, G. H. McKinley, K. Varanassi, *Sci. Adv. Mater.*, 5, 1 (2013)]. Despite the fact that the photocatalytic conversion of $CO_2$ is technically simple, economically viable, and environmentally friendly, several constraints such as narrow absorption range, high electron-hole recombination, low $CO_2$-photocatalyst affinity, and complicated backward reactions limit the conversion efficiency of photocatalytic conversion processes. So, the challenge lies in the selection of suitable photocatalytic materials that provide an improved $CO_2$-photocatalyst affinity, suitable band-gap energy, and a reduced electron-hole recombination. Fabricating a semiconducting material with these properties not only can lead up to the desired photoreaction products but also enhances the efficiency of the production yield. An advantage of using laser induced photocatalysis is that the photon utilization efficiency of any chemical process increases due to the characteristic high intensity of the beam. As a result, the cost of producing a product using of a laser induced photocatalysis is considerably lower than the cost of producing the same product using conventional photon sources.

Various photocatalysts have been developed and applied for photocatalytic reduction of $CO_2$ to methanol, for example photocatalysts that include ubiquitous titania [C. S. Wu Jeffrey, Hung-Ming Lin, 7, 115 (2005)], titania based doped/composite catalysts [H. Liu, A. Q. Dao, C. Fu, *J. Nanosci. Nanotechnol.*, 16, 3437 (2016); J. Maoa, T. Penga, X. Zhanga, K. Lia, L. Zana, *Catal. Commun.*, 28, 38 (2012); H. Tseng, W. C. Chang, J. C. S. Wu, *Appl. Catal., B.* 37, 37 (2002); G. R. Dey, A. D. Belapurkar, K. Kishore, *J. Photochem. Photobiol. A Chem.*, 163, 503 (2004)], and also photocatalysts that include indium doped onto oxides of niobium and tantalum [Z. Zou, J. Ye, H. Arakawa, *Chem. Phys. Lett.* 332, 271 (2000); Z. Zou, J. Ye, H. Arakawa, *Mater. Res. Bull.* 36, 1185 (2001)]. Chen et al. have successfully synthesized an $InTaO_4$ photocatalyst using an aqueous sol-gel method [H. C. Chen, H. C. Chou, J C S Wu, H Y Lin, *J. Mater. Res.* 23 1364 (2008)]. The $InTaO_4$ photocatalyst was further doped with NiO, and the resulting photocatalyst was used for photocatalytic reduction of $CO_2$ into methanol [Z. Y. Wang, H. C. Chou, J. C. S. Wu, D. P.

Tsai, G. Mul, *Appl. Catal. A Gen.*, 380, 172 (2010)]. In some separate studies, silicon carbide and silicon doped $TiO_2$ were used for photocatalytic reduction of $CO_2$ into methanol [M. A. Gondal, M. A. Ali, M. A. Dastageer, X. Chang, *Catal. Lett.* 143, 108 (2013); L. Yousong, J. Guangbin, M. A. Dastageer, Z. Lei, W. Junyi, Z. Bin, X. Chang, M. A. Gondal, *RSC Adv.* 4, 56961 (2014)], and metal oxide loaded $WO_3$ was used as the photocatalyst in the UV region [P. Maruthamuthu, M. Ashokkomar, K. Gurunathan, E. Subramanian, M. V. C. Shastri, *Int. J. Hydrogen Ener.* 14, 525 (1989); P. Maruthamuthu, M. Ashokkomar, *Int. J. Hydrogen Ener.*, 14, 275 (1989)].

Indium oxide ($In_2O_3$) is an n-type direct band-gap semiconductor with the band-gap energy ranging from 2.9 eV to 3.55 eV. Indium oxide possesses high level of optical transparency in the visible light region [X. Sun, Y. Shi, H. Ji, X. Li, S. Cai, C. Zheng, *J. Alloys Compd.* 545, 5 (2012); X. Liu, R. Wang, T. Zhang, Y. He, J. Tu, X. Li. *Sens. Actuator B-Chem.* 150, 442 (2010)]. Indium oxide is widely used in gas sensor applications, since it is very sensitive to certain gases, and the semiconductor-gas interaction can be enhanced by increasing the surface area of the synthesized material [X. Sun, Y. Shi, H. Ji, X. Li, S. Cai, C. Zheng, *J. Alloys Compd.* 545, 5 (2012); X. Liu, R. Wang, T. Zhang, Y. He, J. Tu, X. Li. *Sens. Actuator B-Chem.* 150, 442 (2010)]. The increased surface area causes the creation of more active sites on the material surface, and consequently leads to a change in the semiconductor surface states. The importance of enhancing the surface area of the oxides has been emphasized by several reports that investigated the semiconductor photocatalysts [R Kumar, G Kumar, A Umar, *Nanoscience and Nanotechnology Letters* 6, 631 (2008); G Kumar, R Kumar, S W Hwang, A Umar, *Journal of nanoscience and nanotechnology* 14, 7161 (2014); Peng Liang, Lin Zhang, Xiaoliang Zhao, Jianjiang Li, Long Liu, Rongsheng Cai, Dongjiang Yang, Ahmad Umar, *Sci. Adv. Mater.*, 7, 295 (2015)]. The success of using $In_2O_3$ nanoparticles and nanowires as sensitive gas sensors for oxygen, $CO_2$, $C_2H_5OH$ vapor, and $NO_2$ [Peng Liang, Lin Zhang, Xiaoliang Zhao, Jianjiang Li, Long Liu, Rongsheng Cai, Dongjiang Yang, Ahmad Umar, *Sci. Adv. Mater.*, 7, 295 (2015)] encouraged researchers to synthesize $In_2O_3$ nanoparticles with specific size and shape for various gas related applications. As it is evident from various research reports, monodispersed spherical $In_2O_3$ nanoparticles and nanotubes with the size of 4 nm to 20 nm have been synthesized [Peng Liang, Lin Zhang, Xiaoliang Zhao, Jianjiang Li, Long Liu, Rongsheng Cai, Dongjiang Yang, Ahmad Umar, *Sci. Adv. Mater.*, 7, 295 (2015); X. Lai, H. Wang, D. Mao, N. Yang, J. Yao, C. Xing, D. Wang, X. Li, *Mater. Lett.* 62, 3868 (2008)]. Also, $In_2O_3$ octahedral nanoparticles, nanofibers, and large aggregated nanostructures were synthesized by solution and vapor phase techniques and the synthesis of long indium oxide nano-rod and nanowire arrays with length in the order of ~100 nm to µm were carried out by the use of anodic aluminum oxide membrane templates [X. Lua, L. Yina, *J. Mater. Sci. Tech.* 27, 680 (2011); K. C. Lo, H. P. Ho, K. Y. Fu, P. K. Chu, *Surface & Coatings Technology* 201, 6816 (2007); M. Amith, B. Anirudha, V. J. Leppert, S. H. Risbud, I. M. Kennedy, H. W. H. Lee, *Nano Letters*, 1, 287 (2001); F. Chen, A. H. Kitai, *J. Nanosci. Nanotechnol.* 8, 4488 (2008)].

In view of the forgoing, one objective of the present disclosure is to provide a method of forming methanol by irradiating a mixture containing carbon dioxide, water, and a photocatalyst with UV light to photo-catalytically reduce the carbon dioxide to form methanol. The photocatalyst comprises non-templated indium-oxide nanoparticles and/or templated indium-oxide nanoparticles.

BRIEF SUMMARY OF THE INVENTION

According to a first aspect, the present disclosure relates to a method of forming methanol, involving irradiating a mixture comprising water, carbon dioxide, and a photocatalyst with UV light to reduce the carbon dioxide thereby forming methanol, wherein the photocatalyst comprises non-templated indium-oxide nanoparticles and/or templated indium-oxide nanoparticles.

In one embodiment, the irradiating is carried out without added hydrogen gas.

In one embodiment, the mixture has a temperature in the range of 10 to 40° C. during the irradiating.

In one embodiment, the templated indium-oxide nanoparticles contain cubic nanocrystals having a crystallite size ranging from 50 to 80 nm, wherein the cubic nanocrystals are arranged in an ordered structure.

In one embodiment, the templated indium-oxide nanoparticles have a specific surface area in the range of 30 to 80 $m^2/g$, a specific pore volume in the range 0.08 to 0.15 $cm^3/g$, and an average pore size in the range of 1 to 10 nm.

In one embodiment, the templated indium-oxide nanoparticles have a band gap energy in the range of 2.9 to 3.3 eV.

In one embodiment, the non-templated indium-oxide nanoparticles contain cubic nanocrystals having a crystallite size ranging from 80 to 120 nm, wherein the cubic nanocrystals are randomly arranged.

In one embodiment, the non-templated indium-oxide nanoparticles have a specific surface area in the range of 2 to 10 $m^2/g$, a specific pore volume in the range 0.01 to 0.05 $cm^3/g$, and an average pore size in the range of 10 to 40 nm.

In one embodiment, the non-templated indium-oxide nanoparticles have a band gap energy in the range of 3.1 to 3.5 eV.

In one embodiment, the photocatalyst includes the non-templated indium-oxide nanoparticles and the templated indium-oxide nanoparticles, wherein a weight ratio of the non-templated indium-oxide nanoparticles to the templated indium-oxide nanoparticles is in the range of 10:1 to 1:10.

In one embodiment, the photocatalyst consists of the templated indium-oxide nanoparticles.

In one embodiment, the method further comprises injecting carbon dioxide into the mixture at a pressure in the range of 10 to 80 psi during the irradiating.

In one embodiment, the UV light has a wavelength in the range of 150 to 300 nm.

In one embodiment, the UV light is in a form of a single-frequency laser beam with a wavelength in the range of 150 to 300 nm.

In one embodiment, the mixture is irradiated with UV light for at least 1 hour but no more than 3 hours.

In one embodiment, the method further involves stirring the mixture during the irradiating.

In one embodiment, the photocatalyst includes the templated indium-oxide nanoparticles, wherein a methanol yield is in the range of 400 to 600 µmol·$h^{-1}$ per gram of the photocatalyst.

In one embodiment, the photocatalyst includes the templated indium-oxide nanoparticles, wherein a conversion efficiency of carbon dioxide to methanol is in the range of 30% to 60% by mole relative to an amount of carbon dioxide, and wherein a quantum efficiency of forming methanol is in the range of 1.0% to 10.0% by mole relative to an amount of photons absorbed.

In one embodiment, the photocatalyst includes the non-templated indium-oxide nanoparticles, wherein a methanol yield is in the range of 400 to 500 $\mu mol \cdot h^{-1}$ per gram of the photocatalyst.

In one embodiment, the photocatalyst includes the non-templated indium-oxide nanoparticles, wherein a conversion efficiency of carbon dioxide to methanol is in the range of 30 to 45% by mole relative to an amount of carbon dioxide, and wherein a quantum efficiency of forming methanol is in the range of 1.0 to 4.0% by mole relative to an amount of photons absorbed.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3A is a FE-SEM micrograph of the non-templated indium-oxide nanoparticles ($In_2O_3$—N).

FIG. 3B is a magnified FE-SEM micrograph of the non-templated indium-oxide nanoparticles ($In_2O_3$—N).

FIG. 3C is a FE-SEM micrograph of the templated indium-oxide nanoparticles ($In_2O_3$-T).

FIG. 3D is a magnified FE-SEM micrograph of the templated indium-oxide nanoparticles ($In_2O_3$-T).

FIG. 4A represents $N_2$ adsorption-desorption isotherm of the non-templated indium-oxide nanoparticles ($In_2O_3$—N).

FIG. 4B represents pore volume vs. pore diameter of the non-templated indium-oxide nanoparticles ($In_2O_3$—N).

FIG. 4C represents $N_2$ adsorption-desorption isotherm of the templated indium-oxide nanoparticles ($In_2O_3$-T).

FIG. 4D represents pore volume vs. pore diameter of the templated indium-oxide nanoparticles ($In_2O_3$-T).

FIG. 4E represents $N_2$ adsorption-desorption isotherm of the templating agent (SBA-15).

FIG. 4F represents pore volume vs. pore diameter of the templating agent (SBA-15).

DETAILED DESCRIPTION OF THE EMBODIMENTS

Figure 1:
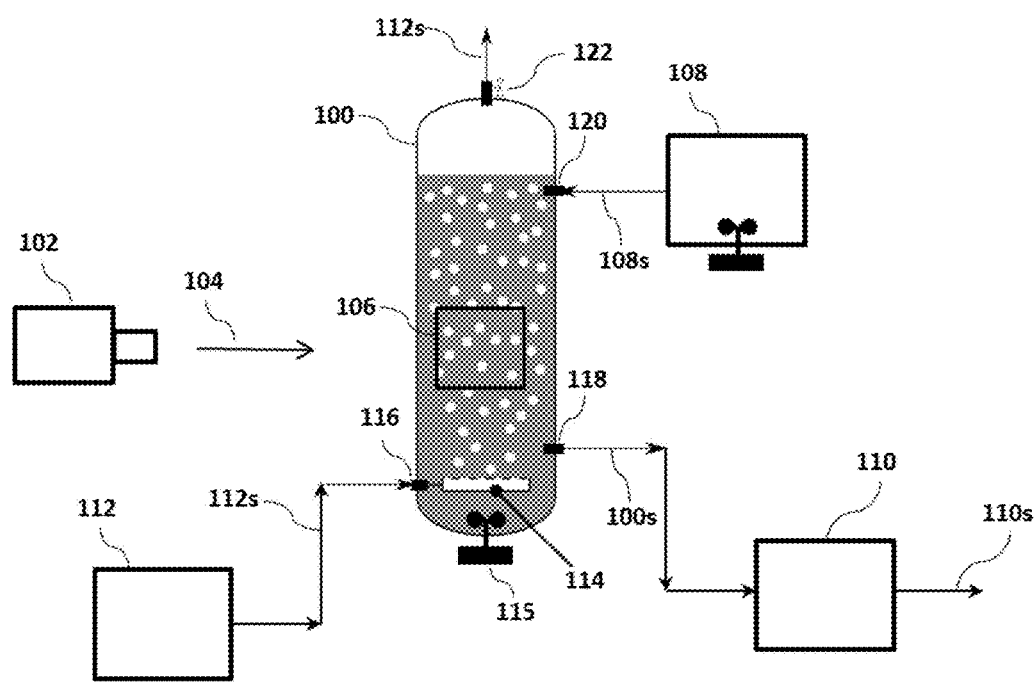
FIG. 1 is a schematic representation of a system for forming methanol.

Referring now to the drawings, wherein like reference numerals designate identical or corresponding parts throughout the several views.

According to a first aspect, the present disclosure relates to a method of forming methanol. The method involves irradiating a mixture comprising water, carbon dioxide, and a photocatalyst with UV light to reduce the carbon dioxide thereby forming methanol.

Preferably, the water used to form the mixture is distilled water, preferably distilled-deionized water, although in some embodiments, the water may come from other sources e.g. a sea, a bay, a river, a lake, a swamp, a pond, a pool, a fountain, a bath, a water treatment plant, a desalination plant, a power plant, etc. In the embodiments where the water comes from said sources, the water may be pre-processed, for instance, by filtering through a coarse filter to remove large particulate matter, and/or by exposure to UV light or ozone.

The term "photocatalyst" as used in this disclosure refers to particulate semiconducting materials that catalyze splitting of water molecules and reducing carbon dioxide by absorbing light photons to generate electron-hole pairs. The photocatalyst includes non-templated indium-oxide nanoparticles and/or templated indium-oxide nanoparticles. In some embodiments, a weight ratio of the non-templated indium-oxide nanoparticles to the templated indium-oxide nanoparticles is in the range of 10:1 to 1:10, preferably 5:1 to 1:9, preferably 3:1 to 1:8, preferably 2:1 to 1:7. Preferably, in some other embodiments, the photocatalyst consists of templated indium-oxide nanoparticles.

The term "templated indium-oxide nanoparticles" as used in this disclosure refers to cubic (or quasi-cubic) nanocrystals with a crystallite size ranging from 50 to 80 nm, preferably 55 to 78 nm, preferably 60 to 75 nm, preferably about 70 nm, wherein the cubic (or quasi-cubic) nanocrystals are arranged in an ordered structure. The cubic (or quasi-cubic) nanocrystals are shown in SEM micrographs of the templated indium-oxide nanoparticles in FIGS. 3C and 3D. The term "ordered structure" as used herein refers to a regular structure which is obtained by a templating agent having an ordered structure, e.g., hollow hexagonal or hollow octagonal, etc. when the nanoparticles are formed via a "hard template" process, as described in this disclosure. Accordingly, indium-oxide nanoparticles may be deposited on at least a portion of the external surface area of the templating agent, and after removing the templating agent, the indium-oxide nanoparticles may be arranged in an ordered structure, e.g., nanowire morphologies provided by the templating agent. Since arrangements of indium-oxide nanoparticles may be carried out in molecular scale dimensions, it may not be observable in the SEM micrographs of FIGS. 3A, 3B, 3C, and 3D.

As shown in the SEM micrographs in FIGS. 3C and 3D, the size of the templated indium-oxide nanoparticles may vary in the range of 1 to 1,000 nm, preferably 5 to 600 nm, preferably 10 to 500 nm, preferably 50 to 400 nm. Other than the cubic (or quasi-cubic) geometry, the templated indium-oxide nanoparticles may be solid spherical, cylindrical, disk-shape, hollow spherical, hollow cylindrical, ellipsoidal, oblong, ovoid, prismatic, etc.

The term "non-templated indium-oxide nanoparticles" as used in this disclosure refers to cubic (or quasi-cubic) nanocrystals with a crystallite size ranging from 80 to 120 nm, preferably 85 to 115 nm, preferably 90 to 110 nm, preferably about 100 nm, wherein the cubic (or quasi-cubic) nanocrystals are randomly arranged without forming an ordered structure. The cubic (or quasi-cubic) nanocrystals are shown in SEM micrographs of the non-templated indium-oxide nanoparticles in FIGS. 3A and 3B. The non-templated indium-oxide nanoparticles may be obtained via a "soft template" process, and without using a templating agent. As shown in the SEM micrographs in FIGS. 3A and 3B, the size of the non-templated indium-oxide nanoparticles may be slightly bigger than the size of the templated indium-oxide nanoparticles. Accordingly, an average size of the non-templated indium-oxide nanoparticles may vary in the range of 1 to 2,000 nm, preferably 50 to 1,500 nm, preferably 100 to 1,200 nm, preferably 200 to 1,000 nm. Other than the cubic (or quasi-cubic) geometry, the non-templated indium-oxide nanoparticles may be solid spherical, cylindrical, disk-shape, hollow spherical, hollow cylindrical, ellipsoidal, oblong, ovoid, prismatic, or some other shape.

Figure 2:
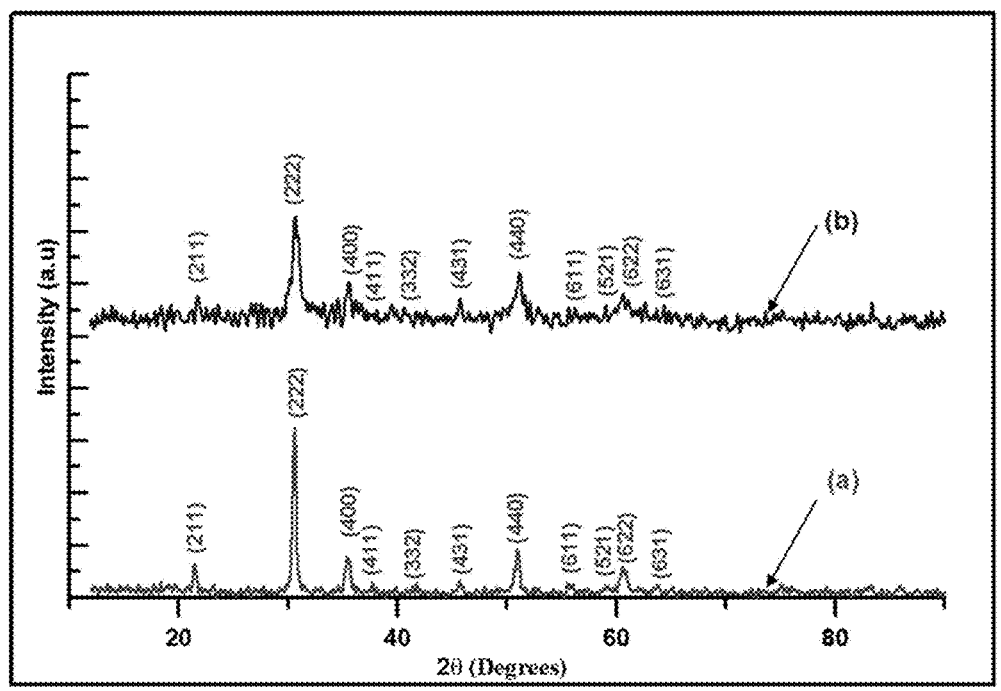
FIG. 2 represents XRD patterns of (a) non-templated indium-oxide nanoparticles ($In_2O_3$—N) and (b) templated indium-oxide nanoparticles ($In_2O_3$-T).

The size of the templated or non-templated indium-oxide nanoparticles (i.e. the size of the cubic or quasi-cubic nanocrystals) is different than the crystallite size. The term "crystallite" as used in this disclosure refers to sub-particulate structural elements that are held together thereby forming a single indium-oxide nanoparticle (templated or non-templated). The crystallite size may be measured from the XRD spectra of the templated or non-templated indium-oxide nanoparticles, as shown in FIG. 2, using Scherrer equations [M. A. Gondal, M. A. Ali, X. F. Chang, K. Shen, Q. Y. Xu, Z. H. Yamani. *J. Environ. Sci. Health A Tox. Hazard. Subs.t Environ. Eng.* 47, 1571 (2012), incorporated herein by reference in its entirety].

One aspect of the present disclosure relates to a method of producing the templated indium-oxide nanoparticles, also referred to as a "hard template" process. First, a suspension that includes a templating agent and an alcohol is sonicated, preferably ultra-sonicated at a temperature in the range of 10 to 50° C., preferably 20 to 40° C., preferably 25 to 30° C., for 1 to 3 hours, preferably about 2 hours. The templating agent is preferably SBA-15 and the alcohol is preferably ethanol. Although in some other embodiments, other templating agents, e.g., MCM-41, ZSM-5, etc. may be used. Indium nitrate and/or hydrates thereof may further be mixed with the suspension and stirred for at least 2 hours, preferably 3 to 5 hours, preferably about 4 hours. A weight ratio of the templating agent to the indium nitrate and/or hydrates thereof may be in the range of 2:1 to 1:10, preferably 1:1 to 1:5, preferably 1:1.5 to 1:4, preferably about 1:2. The suspension may be dried at a temperature of 30 to 70° C., preferably 40 to 60° C., preferably about 45, for 8 to 12 hours, preferably about 10 hours, wherein a dry powder is formed. The dry powder may further be calcined at a temperature of 500 to 700° C., preferably 550 to 650° C., preferably about 600, for 2 to 6 hours, preferably about 4 hours. The dry powder may be treated with a sodium hydroxide solution with a molar concentration of 1.5 to 3.0 M, preferably 2.0 to 2.5 M, preferably about 2.0 M, at a temperature of 50 to 100° C., preferably 60 to 90° C., preferably 70 to 90° C., for 20 to 30 hours, preferably about 24 hours to remove the templating agent, which is preferably SBA-15, and to form the templated indium-oxide nanoparticles. The templated indium-oxide nanoparticles may be washed with deionized water, centrifuged, and thermally dried at a temperature of 50 to 70° C., preferably about 60° C. The non-templated indium-oxide nanoparticles may preferably be produced with substantially the same procedure and without the incorporation of the templating agent, also referred to as a "soft template" process.

Structural differences between the templated indium-oxide nanoparticles and non-templated indium-oxide nanoparticles may be attributes to the way these nanoparticles are synthesized, i.e. the presence or the absence of the templating agent. Accordingly, the templated indium-oxide nanoparticles and non-templated indium-oxide nanoparticles may be mesoporous or microporous. In some embodiments, a specific (BET) surface area of the templated indium-oxide nanoparticles is in the range of 30 to 80 $m^2/g$, preferably 40 to 70 $m^2/g$, preferably 50 to 60 $m^2/g$, whereas the specific (BET) surface area of the non-templated indium-oxide nanoparticles is in the range of 2 to 10 $m^2/g$, preferably 3 to 5 $m^2/g$, preferably 3.5 to 4.5 $m^2/g$. In addition, a specific pore volume of the templated indium-oxide nanoparticles is in the range of 0.08 to 0.15 $cm^3/g$, preferably 0.09 to 0.14 $cm^3/g$, preferably 0.10 to 0.13 $cm^3/g$, whereas the specific pore volume of the non-templated indium-oxide nanoparticles is in the range of 0.01 to 0.05 $cm^3/g$, preferably 0.02 to 0.04 $cm^3/g$, preferably 0.02 to 0.03 $cm^3/g$. Furthermore, an average pore size of the templated indium-oxide nanoparticles is in the range of 1 to 10 nm, preferably 2 to 9 nm, preferably 3 to 8 nm, preferably 4 to 7 nm, whereas the average pore size of the non-templated indium-oxide nanoparticles is in the range of 10 to 40 nm, preferably 15 to 35 nm, preferably 20 to 30 nm, preferably 22 to 26 nm.

In one embodiment, average band-gap energy of the templated indium-oxide nanoparticles ranges from 2.9 to 3.3 eV, preferably from 3.0 to 3.2 eV, preferably about 3.1 eV, whereas average band-gap energy of the non-templated indium-oxide nanoparticles ranges from 3.1 to 3.5 eV, preferably from 3.2 to 3.4 eV, preferably about 3.3 eV. The band-gap energy of the photocatalyst (i.e. the templated and/or the non-templated indium-oxide nanoparticles) may be engineered, according to methods known in the art, e.g. incorporation of quantum dots, to be at least about 2 eV, preferably in the range from about 2.0 eV to about 5.0 eV, or from about 2.5 eV to about 4.5 eV, or preferably from about 2.8 eV to about 4.0 eV. A photocatalyst having such a band-gap energy may harness solar light in the UV region. In one embodiment, a valence band edge potential of the templated indium-oxide nanoparticles is in the range of 2.2 to 2.5 V (Volts), preferably 2.3 to 2.4 V, most preferably about 2.38 V, relative to the normal hydrogen electrode (NHE); whereas a conduction band edge potential of the templated indium-oxide nanoparticles is in the range of −0.65 to −0.85 V (Volts), preferably −0.7 to −0.8 V, most preferably about −0.77 V, relative to the NHE. In another embodiment, a valence band edge potential of the non-templated indium-oxide nanoparticles is in the range of 2.3 to 2.6 V, preferably 2.4 to 2.5 V, most preferably about 2.43 V, relative to the NHE; whereas a conduction band edge potential of the templated indium-oxide nanoparticles is in the range of −0.7 to −0.9 V (Volts), preferably −0.75 to −0.85 V, most preferably about −0.8 V, relative to the NHE. In another embodiment, a resistivity of the photocatalyst (i.e. the templated and/or the non-templated indium-oxide nanoparticles) is no more than about $10^{-3}$ Ωm, preferably no more than about $10^{-6}$ Ωm, preferably no more than about $10^{-7}$ Ωm, preferably between about $10^{-14}$ Ωm and about $10^{-10}$ Ωm, preferably between about $10^{-12}$ Ωm and about $10^{-6}$ Ωm.

In one embodiment, the photocatalyst may further include at least one material selected from the group consisting of zinc oxide, gallium nitride, tin dioxide, magnesium oxide, tungsten trioxide, nickel oxide, titanium oxide, copper oxide, cerium oxide, zirconium oxide, aluminum oxide, and iron oxide. In one embodiment, the photocatalyst further includes at least one element such as, without limitation, Si, Zr, Ce, Y, Nd, Sb, Li, Sr, Ba, Ru, Ta, Mo, Cr, Ti, W, Sn, Al, V, Fe, Co, Ni, Cu, Zn, Rh, Pd, Ag, Pt, and Au, and/or other metal compounds containing one of those metals and one or more non-metal elements.

In one embodiment, the photocatalyst may include quantum dots. The "quantum dots" as used herein refer to tiny semiconducting particles having diameters in the range of 1 to 50 nm, preferably 2 to 40 nm, more preferably 5 to 30 nm. The quantum dots may be added to adjust electronic properties (e.g. band-gap energy) of the photocatalyst. The quantum dots may be one or more of core-type quantum dots, core-shell quantum dots, and alloyed quantum dots. Exemplary quantum dots, without limitation, include chalcogenides (i.e. selenides or sulfides) of metals, e.g., CdSe, ZnSe, CdSs/ZnS, CdS/ZnS, CdTe, PbS, InP/ZnS, PbSe, etc.

The photocatalyst may further include a dye that is deposited on the surface of the photocatalyst. The dye may be utilized to enhance the absorption of UV light photons onto the photocatalyst. The dye may an azin dye, an azo dye, a diarylmethane dye, a fluorescent dye, a food coloring, a fuel dye, an ikat dye, an indigo structured dye, an indophenol dye, a perylene dye, a phenol dye, a quinoline dye, a rhodamine dye, a solvent dye, a staining dye, a thiazine dye, a thiazole dye, a triarylmethane dye, a vat dye, a violanthrone dye, etc. For example, in one embodiment, the dye is a thiazine dye, in particular, methylthioninium chloride (methylene blue).

In one embodiment, the photocatalyst may be present as agglomerates. As used herein, the term "agglomerates" refers to clusters or clumps of the templated and/or non-templated indium-oxide nanoparticles and optionally other materials, quantum dots, and/or dyes, primary particles. These clusters or clumps of the templated and/or non-templated indium-oxide nanoparticles may have an average diameter of at least 2 times, preferably at least 3 times, but preferably no more than 5 times the average diameter of the templated and/or non-templated indium-oxide nanoparticles. Accordingly, an average diameter of the agglomerates may be in the range of 100 nm to 10 μm, preferably 500 nm to 5 μm, more preferably 1 to 3 μm. As used in this disclosure, the term "agglomerate" is different that the term "crystallite," as the term "agglomerate" refers to an aggregate of templated and/or non-templated indium-oxide nanoparticles, whereas the term "crystallite" refers to an aggregate of sub-particulate structural elements that form a single indium-oxide nanoparticle (templated or non-templated).

Referring now to FIG. 1. Once the photocatalyst is prepared, it may be mixed with water and carbon dioxide. Preferably, the photocatalyst may first be mixed with water to form the mixture, and carbon dioxide may further be injected into the mixture. In one embodiment, water and the photocatalyst are mixed in a mixer 108 to form the mixture. A mass concentration of the photocatalyst in the mixture is in the range of 0.1 to 100 g/L (i.e. gram of the photocatalyst per one liter of the mixture), preferably 0.5 to 10 g/L, preferably 1.0 to 5.0 g/L, preferably about 3.0 g/L.

Preferably, the mixture may be delivered to a vessel 100 for mixing with carbon dioxide. Carbon dioxide may be mixed with the mixture using various methods known to those skilled in the art. For example, in a preferred embodiment, carbon dioxide is injected to the mixture. Preferably, the mixture has a standard temperature and pressure, i.e. a temperature in the range of 10 to 40° C., preferably 15 to 35° C., preferably 20 to 30° C., and a pressure in the range of 0.8 to 1.2 atm, preferably 0.9 to 1.1 atm, preferably 0.95 to 1.05 atm. Accordingly, formation of methanol from carbon dioxide is taken place in the standard temperature and pressure, and thus the cost of producing one cubic meter of methanol is at least 50%, preferably at least 70%, preferably at least 90% lower than the cost of producing methanol using conventional methods.

The mixer 108 is located upstream of the vessel 100 and fluidly connected to the vessel via a liquid inlet 120. Water may be continuously mixed with the photocatalyst in the mixer and agitated thoroughly to form the mixture 108s. The mixer 108 may optionally be utilized to store the mixture and feed the mixture 108s to the vessel 100 when needed. Preferably, the mixture may be stored in relatively dark conditions in the mixer with an illuminance of no more than 0.001 lux, preferably no more than 0.0001 lux, even more preferably no more than 0.00001 lux. In addition, the vessel 100 has an internal cavity, which may be cylindrical, rectangular, spherical, etc. and may be made of a material including, but not limited to, stainless steel, galvanized steel, mild steel, aluminum, copper, brass, bronze, iron, nickel, titanium, quartz, glass, polypropylene, polyvinyl chloride, polyethylene, and/or polytetrafluoroethylene. Preferably, the vessel 100 may be made of stainless steel such as type 304, 316, or 316L stainless steel. Alternatively, the vessel 100 may be made of an austenitic chromium-nickel stainless steel doped with 2 to 3 wt % molybdenum. The vessel 100 may have a wall thickness of 0.1 to 3 cm, preferably 0.1 to 2 cm, more preferably 0.2 to 1.5 cm. The volume of the internal cavity of the vessel 100 may be different according to the scale of methanol production. For example, for small scale or benchtop productions, the internal cavity may have a volume of 100 mL-50 L, preferably 1 L-20 L, more preferably 2 L-10 L. For pilot plant productions, the internal cavity may have a volume of 50 L-10,000 L, preferably 70 L-1,000 L, more preferably 80 L-2,000 L. For industrial-scale manufacturing plants, the internal cavity may have a volume of 10,000 L-500,000 L, preferably 20,000 L-400,000 L, more preferably 40,000 L-100,000 L. In the embodiments where the vessel 100 is made of a non-transparent material, an additional opening, e.g. a transparent window 106, may be adjusted in the vessel wall. The transparent window 106 may comprise quartz, glass, or a polymeric material transparent to UV light 104 such as poly(methyl methacrylate), polyethylene, and/or polypropylene. As defined herein, the term "transparent" refers to an optical quality of a compound wherein a certain wavelength or range of wavelengths of light may traverse through a portion of the compound with a small loss of light intensity. Here, the transparent window 106 may causes a loss of less than 10%, preferably less than 5%, more preferably less than 2% of the intensity of a wavelength of UV light 104. In one embodiment, the vessel wall and the transparent window may comprise the same material, for example, a vessel may comprise poly(methyl methacrylate) walls, which may also function as transparent windows. Additionally, the vessel 100 may be equipped with a safe valve 122 to prevent accumulation of carbon dioxide and excessive pressure in the overhead section of the vessel.

Devices to measure and record the physical and/or chemical properties of carbon dioxide, methanol, and/or the mixture may be connected to vessel. Examples of these devices include, but are not limited to, pressure gauges, flowmeters, conductivity meters, pH meters, temperature sensors, composition analyzers, and spectrophotometers. Recorded data from a device may allow a user skilled in the art to calculate reaction parameters, such as methanol yield and quantum efficiency, reaction conversion, methanol concentration, photoluminescence behavior of the photocatalyst, etc.

Carbon dioxide may be transported to the vessel 100 from a coal plant as a byproduct obtained from combusting a fossil fuel, e.g., coal, oil, and/or gas. Alternatively, the carbon dioxide may be transported from industrial production processes, such as mineral production processes, metal production processes, petrochemical processes, power plants, etc. Alternatively, carbon dioxide 112s may be delivered from an upstream $CO_2$ storage tank 112 to the internal cavity of the vessel 100 via a gas inlet 116, as shown in FIG. 1.

In some embodiments, carbon dioxide may be continuously injected (or purged) into the mixture at an injection rate in the range of 1 to 50 mL/min, preferably 2 to 30 mL/min, preferably 3 to 20 mL/min, preferably about 10 mL/min. In larger scale applications, the injection rate may be in the range of 50 to 10,000 mL/min, preferably 100 to 1,000 mL/min, preferably 150 to 500 mL/min. The carbon dioxide may be injected at a pressure of at least 10 psi, preferably at least 20 psi, preferably at least 30 psi. In a preferred embodiment, the carbon dioxide is injected at a pressure in the range of 10 to 80 psi, preferably 20 to 70 psi, preferably 30 to 60 psi, preferably 40 to 50 psi. In a preferred embodiment, the carbon dioxide has a purity of at least 99 vol %, preferably at least 99.5 vol %, preferably at least 99.9 vol %.

In some preferred embodiments, carbon dioxide is injected into the mixture using a perforated tube 114 disposed in the internal cavity of the vessel 100, which is configured to be submerged when the internal cavity is filled with the mixture. The perforated tube 114 may inject/bubble carbon dioxide into the mixture; while simultaneously agitate the mixture to prevent formation of photocatalyst agglomerates or disintegrate the agglomerates present in the mixture. The perforated tube 114 may have a rectangular shape (i.e. having a rectangular cross section), or a rounded tubing (i.e. having a rounded cross section such as circular or elliptical). Depending on the shape of the vessel, the perforated tube may be extended straight or preferably extended helically in the internal cavity the vessel. Perforations of the perforated tube may be equally spaced apart around the circumference and along the length of the perforated tube. Carbon dioxide may alternatively be injected into the mixture using a nozzle, a sprinkler, a gas spray, or other means known to those skilled in the art.

After mixing carbon dioxide, the mixture is irradiated with a UV light 104 in order to photo-catalytically split water molecules and to further reduce carbon dioxide to produce methanol. Preferably, the UV light 104 has a wavelength in the range of 150 to 300 nm, preferably 180 to 280 nm, preferably 250 to 270 nm. Although this wavelength ranges of the UV light is not meant to be limiting and UV light outside this range may also be utilized. In addition, other light sources such as infrared, microwave, visible light, X-ray, γ-ray, etc. may also be utilized. In one embodiment, the intensity of the UV light 104 is in the range of 450 to 1550 mW/cm$^2$, preferably 600 to 1400 mW/cm$^2$, more preferably 800 to 1200 mW/cm$^2$. In another embodiment, the UV light 104 provides sufficient energy that is equivalent to or greater than the band-gap energy of the photocatalyst.

In the most preferred embodiment, the UV light 104 is in a form of a single-frequency laser beam or a pulsed single-frequency laser beam with a wavelength in the range of 150 to 300 nm, preferably 180 to 280 nm, preferably 250 to 270 nm, more preferably 265 to 267 nm, most preferably about 266 nm. In another preferred embodiment, the UV light 104 is in a form of a pulsed single-frequency laser beam with a pulse energy in the range of 20 to 80 mJ (milli Joules), preferably 30 to 60 mJ, preferably 35 to 45 mJ; and a pulse width in the range of 2 to 20 ns (nano seconds), preferably 5 to 15 ns, preferably 7 to 10 ns.

The UV light 104 may be irradiated from a light source 102, preferably a UV light source, such as a mercury or xenon gas discharge lamp, an electric arc, sunlight, a light emitting diode (LED), a laser, a fluorescent lamp, a cathode ray tube, etc. In one embodiment, filters, reflectors, collimators, fiber optics, polarizers, and/or lenses may be used to manipulate the light path or properties of the UV light from the light source 102. For example, one or more reflectors may be used to focus the light from a mercury gas discharge lamp onto the mixture. In one embodiment, two or more light sources may be used, which may be of the same type or different types. In the embodiments where sunlight is used as a light source, the sunlight may be filtered, reflected, and focused onto the mixture to increase the proportion of UV light intensity while minimizing radiation from other wavelength ranges. For instance, a glass optical filter may be used to allow UV light to pass while blocking other wavelengths.

In some embodiments, the light source is located inside the vessel and may or may not be submerged into the mixture. These embodiments may particularly be useful when an additional opening, e.g. a transparent window, is not adjusted in the vessel wall. In the embodiments where the light source is submerged into the mixture, the light source may be equipped with a waterproof coating or some other protective covering. These embodiments are not shown in FIG. 1.

In some embodiments, at least a portion of vessel may be temperature-regulated to prevent overheating and/or evaporation of water in the mixture, for example, by water tubing, a water and/or ice bath, ice packs, heat sinks, air cooling, or other methods known to those skilled in the art. Accordingly, a temperature of the mixture is preferably maintained at a temperature in the range of 10 to 40° C., preferably 15 to 35° C., preferably 20 to 30° C., during UV irradiation.

Figure 8:
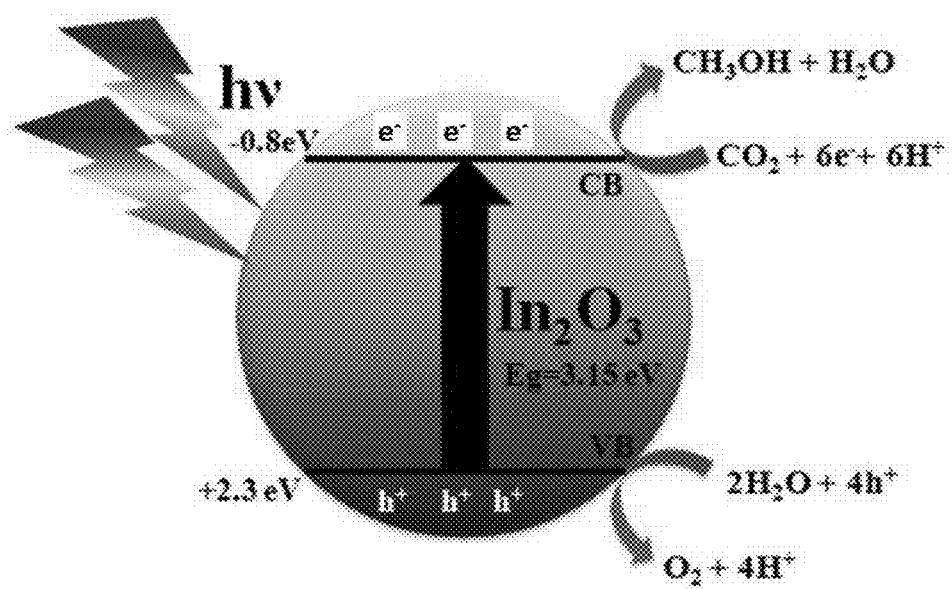
FIG. 8 depicts a diagram of photocatalytic conversion of $CO_2$ into methanol.

Exposure of the photocatalyst to the UV light irradiation may excite electrons of the photocatalyst into the conduction band; while correspondingly generate holes in the valence band of the photocatalyst. The oxidation power of the holes (h$^+$) may lead to oxidize and therefore split water molecules, thereby forming protons (i.e. H$^+$). On the other hand, the reduction power of the excited electrons may lead to reduce carbon dioxide in the presence of the protons, thereby forming methanol. Photocatalytic redox reaction mechanisms and the corresponding standard reduction potential are represented in FIG. 8, as well as in (i), (ii), and (iii).

$$\text{Photocatalyst} + h\nu \rightarrow e^- + h^+ \quad \text{(i)}$$

$$2H_2O + 4h^+ \rightarrow O_2 + 4H^+ \quad E°_{redox} = +0.82 \text{ V} \quad \text{(ii)}$$

$$CO_2 + 6H^+ + 6e^- \rightarrow CH_3OH + H_2O \quad E°_{redox} = -0.38 \text{ V} \quad \text{(iii)}$$

A standard reduction potential to initiate oxidation of water to create $H^+$ is at least +0.82 V (Volts) relative to the normal hydrogen electrode (NHE). In addition, a standard reduction potential to initiate reduction of carbon dioxide is at least −0.38 V relative to NHE. Accordingly, in order to make the redox reactions to happen, the valence band (VB) edge potential of the photocatalyst (as shown in FIG. 8) needs to be higher (more positive) than the standard reduction potential of water oxidation, and also the conduction band (CB) edge potential of the photocatalyst (as shown in FIG. 8) needs to be lower (more negative) than the standard reduction potential of reduction of carbon dioxide. In view of that, in the most preferred embodiment, the photocatalyst includes templated and/or non-templated indium-oxide nanoparticles and the UV light is in a form of a pulsed single-frequency laser beam with a wavelength in the range of 250 to 270 nm, more preferably 265 to 267 nm, most preferably about 266 nm, in order to efficiently form methanol from carbon dioxide. A pulsed single-frequency laser beam with a wavelength of 266 nm, a pulse energy of 40 mJ/pulse and a pulse repetition rate of 10 Hz, may irradiate approximately $3.212\times10^{19}$ photons per minute.

Splitting water molecules may form hydrogen radicals other than protons (i.e. $H^+$), for example, in some embodiments, deuterons ($^2H^+$) and/or tritons ($^3H^+$) may also be formed as a result of splitting water molecules. Preferably, a concentration of deuterons ($^2H^+$) and/or tritons ($^3H^+$), when present, is no more than 10,000 ppm, preferably no more than 1,000 ppm, preferably no more than 500 ppm.

In a preferred embodiment, the method of forming methanol does not involve injecting hydrogen gas into the mixture, because the protons that are formed as a result of splitting water molecules may participate in reduction reactions of carbon dioxide. On the other hand, since methanol is formed at standard temperate and pressure without using an external heating source to elevate the temperature of the mixture, the amount of energy per one mole of methanol formed is reduced by at least 50%, preferably at least 80%, preferably at least 90%, when compared to conventional methanol production processes. In view of that, the cost of producing methanol is significantly reduced, for example, by at least 50%, preferably at least 80%, preferably at least 90% when compared to the cost of producing methanol in the conventional methanol production processes.

The UV light 104 may be irradiated into the mixture for at least 30 minutes. Preferably, the UV light is irradiated into the mixture for 1 to 3 hours, preferably 120 to 180 minutes, more preferably about 150 minutes. Preferably, the UV light may not be irradiated into the mixture for more than 4 hours, or more than 3.5 hours, or preferably more than 3 hours.

In a preferred embodiment, the mixture is stirred during UV irradiation in order to prevent formation of photocatalyst agglomerates or disintegrate the agglomerates that are already present in the mixture and to maximize an effective surface area of the photocatalyst. Stirring the mixture may be in a continuous mode during the UV irradiation, or in a time-interval mode. The mixture may be stirred with an agitator 115 that is located inside the vessel 100. The agitator may be a mechanical stirrer, for instance a propellant that is attached to a rotary motor through a shaft, or a magnetic stirrer. A rotatory speed of the agitator, when present, may be no more than 400 rpm, preferably in the range of 5 to 400 rpm, preferably 10 to 300 rpm, preferably 20 to 200 rpm. In the embodiments wherein the vessel 100 is equipped with the perforated tube 114, the agitator may be removed from the vessel.

Reaction parameters of photocatalytic conversion of carbon dioxide to methanol, e.g. a quantum efficiency of forming methanol, a methanol yield, a $CO_2$ conversion efficiency, etc. may depend on the amount of the templated and the non-templated indium-oxide nanoparticles present in the photocatalyst. For example, in some embodiments, the photocatalyst consists of the templated indium-oxide nanoparticles, wherein a methanol yield is in the range of 400 to 600 μmol·h$^{-1}$, preferably 420 to 550 μmol·h$^{-1}$, preferably 440 to 520 μmol·h$^{-1}$, preferably 460 to 500 μmol·h$^{-1}$, per gram of the photocatalyst. Also, according to these embodiments, a conversion efficiency of carbon dioxide to methanol is in the range of 30% to 60% by mole, preferably 40% to 50% by mole, preferably 45% to 48% by mole relative to the number of moles of carbon dioxide mixed with the mixture; and a quantum efficiency of forming methanol is in the range of 1.0% to 10.0% by mole, preferably 3.0% to 6.0% by mole, preferably 4.0% to 5.0% by mole relative to an amount of photons absorbed. In some other embodiments, the photocatalyst consists of the non-templated indium-oxide nanoparticles, wherein a methanol yield is in the range of 400 to 500 μmol·h$^{-1}$, preferably 410 to 480 μmol·h$^{-1}$, preferably 420 to 460 μmol·h$^{-1}$, preferably 430 to 450 μmol·h$^{-1}$, per gram of the photocatalyst. Also, according to these embodiments, a conversion efficiency of carbon dioxide to methanol is in the range of 30% to 60% by mole, preferably 35% to 45% by mole, preferably about 40% by mole relative to the number of moles of carbon dioxide mixed with the mixture; and a quantum efficiency of forming methanol is in the range of 1.0% to 5.0% by mole, preferably 3.0% to 4.0% by mole, preferably about 4.0% by mole relative to an amount of photons absorbed. As used herein, the term "methanol yield" refers to a maximum amount of methanol (in μmol) that is produced in one hour and at the standard temperate and pressure, per one gram of the photocatalyst. The term "conversion efficiency of carbon dioxide to methanol" refers to a ratio of the number of moles (or molar flow rates) of methanol formed to the number of moles (or molar flow rates) of carbon dioxide injected. Also, the term "quantum efficiency of forming methanol" refers to a ratio of the number of moles of methanol formed to the number of photons absorbed onto the photocatalyst (in Einstein, i.e., one Avogadro number of photons).

In a preferred embodiment, the methanol is separated from the mixture via methods known to those skilled in the art. For example, the methanol may be separated via a distillation process, for instance, using a downstream distillation unit 110 that may be fluidly connected with the vessel 100 via a liquid outlet 118. Methanol may be separated from a methanol-rich stream 100s (i.e. the mixture that includes methanol and egresses the vessel) that may be delivered to the distillation unit 110. Methanol may be separated from the methanol-rich stream 100s using other methods known to those skilled in the art, e.g. liquid-liquid extraction, vapor-liquid extraction, cryogenic distillation, and/or any combination thereof. A volumetric concentration of a methanol stream 110s that comes out of the distillation unit 110 may be at least 80% by volume, preferably at least 90% by volume, preferably at least 95% by volume, preferably at least 99% by volume. The methanol may further be purified and be used as a feedstock in various chemical and/or petrochemical processes, e.g., methanol-to-olefin processes, particularly methanol-to-propylene, metathesis, propane dehydrogenation, high severity fluid catalytic cracking, olefin cracking, etc. In view of that, the methanol may be used for manufacturing organic compounds such as formaldehyde, acetic acid, dimethyl ether, methyl tert-butyl ether, ethylene, propylene, biodiesel, etc. Alternatively, the methanol may be used as a diluent for gasoline.

The examples below are intended to further illustrate protocols for the method of forming methanol, and are not intended to limit the scope of the claims.

Example 1—Material Synthesis

Ordered mesoporous $In_2O_3$ nanocrystals ($In_2O_3$-T) were prepared by nanocasting, "hard template" method [X. Lai, H. Wang, D. Mao, N. Yang, J. Yao, C. Xing, D. Wang, X. Li, *Mater. Lett.* 62, 3868 (2008)]. SBA-15 (Sigma Aldrich) was used as hard template in this study. In a typical synthesis, required amount of $In(NO_3)_3 \cdot xH_2O$ was dissolved in ethanol and was subsequently mixed with ultra-sonicated SBA-15 dispersion in ethanol. The resulting mixture was stirred vigorously for 4 hours at room temperature and dried in a furnace at 45° C. overnight. The weight ratio of SBA-15 to $In(NO_3)_3 \cdot xH_2O$ mixture was 1:2. The powder was then thermally decomposed in a quartz glass bottle at 600° C. for 4 hours with 1.0° C./min ramp rate from the room temperature. Finally, the silica template (SBA-15) was removed by dissolving the $In_2O_3$/SBA-15 composite with hot 2 M NaOH and etched at 75° C. for 24 hours. The resulting product was washed with deionized water, recovered by centrifugation and dried at 60° C. The final $In_2O_3$ nanocrystal was light yellow colored powder and was labeled as $In_2O_3$-T. In the case of non-templated indium oxide ($In_2O_3$—N) synthesis, the similar procedure was followed without using SBA-15.

Example 2—Material Characterization

The phase structure of the synthesized materials were analyzed by X-ray diffraction using a Bruker Advance-D8 diffractometer with Cu Kα radiation source (λ=0.1540 nm) with a scanning rate of 2 degrees/minute in the 2° to 90° 2θ angle range. The morphological properties were studied using Lyra TESCAN Field emission electron microscope (FE-SEM) equipped with an energy dispersive X-ray spectrometer (EDS). A micrometrics accelerated surface area and porosimeter (ASAP 2020) system was used to measure nitrogen adsorption-desorption of the catalysts. The system is equipped with dedicated software which uses conventional analysis such as Brunauer-Emmett-Teller (BET) and Barrett-Joyner-Halanda (BJH) methods for the determination of the textural properties, like specific surface area and pore size distribution respectively. The diffused reflectance spectra of the samples were carried out by using Jasco 670 double beam spectrophotometer equipped with the integrator and the photoluminescence spectra of the samples were recorded using Fluorolog FL3-iHR, HORIBA Jobin Yvon which has a xenon lamp as the light source.

Example 3—Photocatalytic Conversion

The detailed experimental system is described in our earlier work [M. A. Gondal, M. A. Ali, X. F. Chang, K. Shen, Q. Y. Xu, Z. H. Yamani. *J. Environ. Sci. Health A Tox. Hazard. Subs.t Environ. Eng.* 47, 1571 (2012), incorporated herein by reference in its entirety]. Photo catalytic reduction of $CO_2$ into methanol was carried out in a specially designed stainless steel reaction cell fitted with quartz windows for UV transmission and various inlet/outlet ports for gas injection and sample dispensing. The light source is the 266 nm pulsed laser beam, which is the fourth harmonic of the Spectra Physics Nd: YAG laser (Model GCR 250) with 40 mJ pulse energy and 8 s pulse width. In the reaction chamber, 300 mg of the catalyst is mixed in 100 mL of water and $CO_2$ gas (99.99% purity) with 45 psi outlet pressure was continuously purged into the mixture. The reaction cell was kept on the magnetic stirrer throughout the process for the vigorous stirring of the mixture. Prior to irradiation with laser, the mixture was stirred for 30 minutes in order to verify the presence of any possible products in the absence of light and in our case, no peak was identified without light radiation. Once the mixture was subjected to irradiation, the sample was extracted from the reactor using a micro syringe at 30 min interval to perform GC analysis.

For the quantification of the product of photochemical reaction, a combined gas chromatograph/mass spectrograph system (GC Agilent 4890D) was used. A 1.5 µL of the liquid extracted from the reactor was injected into the inlet port of the Agilent Rtx-Wax column (30 m×0.32 mm×0.32 mm) with He as the carrier gas and Mass spectrometer and the detector. The oven temperature is at 30° C. while both the temperatures of injector and detector were set at 170° C. The oven temperature is set to increase at the rate of 5° C./min to 100° C. The oven temperature was subsequently decreased from 200° C. to 30° C. to deplete the residual components from the column. The dedicated software of the GC/MS is capable of giving the real time display of the chromatogram and the mass spectrum.

Example 4—X-Ray Diffraction Analysis of $In_2O_3$

XRD patterns of the as prepared $In_2O_3$—N and $In_2O_3$-T nanostructures are depicted in FIG. 2, where the main diffraction peaks for both the samples appear around 21.50°, 30.56°, 35.46°, 51.14° and 60.65° which can be indexed to (211), (222), (400), (440) and (622) cubic plane with lattice parameters 1.011 nm (JCPDS #71-2195) and 1.012 nm (JCPDS #06-0416) respectively. The more prominent additional peaks observed in the case of $In_2O_3$—N in FIG. 2(*a*) is attributed to its more crystalline structure. The crystalline sizes for the $In_2O_3$—N and the ordered mesoporous $In_2O_3$-T are calculated using Scherrer equations [M. A. Gondal, M. A. Ali, X. F. Chang, K. Shen, Q. Y. Xu, Z. H. Yamani. *J. Environ. Sci. Health A Tox. Hazard. Subs.t Environ. Eng.* 47, 1571 (2012)] and their values are around 100 nm and 69.2 nm respectively, while the micro-strains are estimated to be around $4.0 \times 10^{-4}$ nm and $1.94 \times 10^{-2}$ nm, respectively. The observation of larger strain and smaller crystalline size of the $In_2O_3$-T nanocrystals, manifested as the more broadened peaks of the XRD pattern, arise from the dislocation, precipitate or other forms of defect. The defects are induced due to the presence of SBA-15 during the synthesis of $In_2O_3$-T resulted in the creation of more active sites that increases the adsorption ability of the material, which is crucial for the photo catalytic applications of the materials. Hence from the XRD results we expect a better photo catalytic performance of mesoporous $In_2O_3$-T compared to the non-templated $In_2O_3$—N.

Example 5—Morphology and Surface Properties of $In_2O_3$

FIGS. 3A, 3B, 3C, and 3D depict the FE-SEM images showing the surface morphologies of $In_2O_3$-T and $In_2O_3$—N nanostructures, where both the materials are obviously nano-scaled and the particles are well dispersed. Upon comparing the FE-SEM images in FIGS. 3A, 3B, 3C, and 3D, $In_2O_3$—N is quasi nano-cubic with larger grain size and higher crystallinity compared to the mesoporous $In_2O_3$-T nanostructures, which validates the results of x-ray diffraction. Also in the image, the lesser crystalline $In_2O_3$-T nanoparticles are characterized by rougher surfaces, which indicate the increased surface area. In order to further substantiate the results of FESEM, BET and BJH analysis for specific surface areas, pore sizes and pore volumes of the $In_2O_3$-T and $In_2O_3$—N nanomaterials were carried out and the results are summarized in Table 1. The larger specific surface area of 56.05 $m^2/g$ for $In_2O_3$-T nanocrystals from BET analysis as compared to 4.01 $m^2/g$ for $In_2O_3$—N confirms that the former has the smaller particle sizes than $In_2O_3$—N nanocrystals, which substantiate the results of XRD and FESEM. FIGS. 4A, 4B, 4C, 4D, 4E, and 4F show the nitrogen adsorption desorption isotherm for the $In_2O_3$-T and $In_2O_3$—N nanocrystals as well as SBA-15, and the corresponding pore diameter versus pore volume plots. The $In_2O_3$-T show type IV hysteresis loops which is another evidence for the presence of mesopores in $In_2O_3$-T nanocrystals [Peng Liang, Lin Zhang, Xiaoliang Zhao, Jianjiang Li, Long Liu, Rongsheng Cai, Dongjiang Yang, Ahmad Umar, *Sci. Adv. Mater.*, 7, 295 (2015)]. Also the pore volume and the pore size of the materials deduced from the nitrogen adsorption-desorption isotherms are listed in table-1, which further clarifies the mesoporosity of $In_2O_3$-T.

TABLE 1

Calculated BET specific surface area, BJH pore volume, pore sizes, lattice constant, strain and crystallite size of the synthesized catalysts

|  | BET surface area ($m^2g^{-1}$) | BJH pore volume ($cm^3g^{-1}$) | Pore size (nm) | Lattice constant (nm) | Micro-strain | Crystallites (nm) |
|---|---|---|---|---|---|---|
| $In_2O_3$-N | 4.01 | 0.02 | 24.51 | 1.011 | $4.00 \times 10^{-4}$ | 100.00 |
| $In_2O_3$-T | 56.05 | 0.12 | 6.10 | 1.012 | $1.94 \times 10^{-2}$ | 69.23 |
| SBA-15 | 664.77 | 1.05 | 6.07 | — | — | — |

Example 6—Diffused Reflectance Spectrum and Band Gap Energy of $In_2O_3$

Figure 5A:
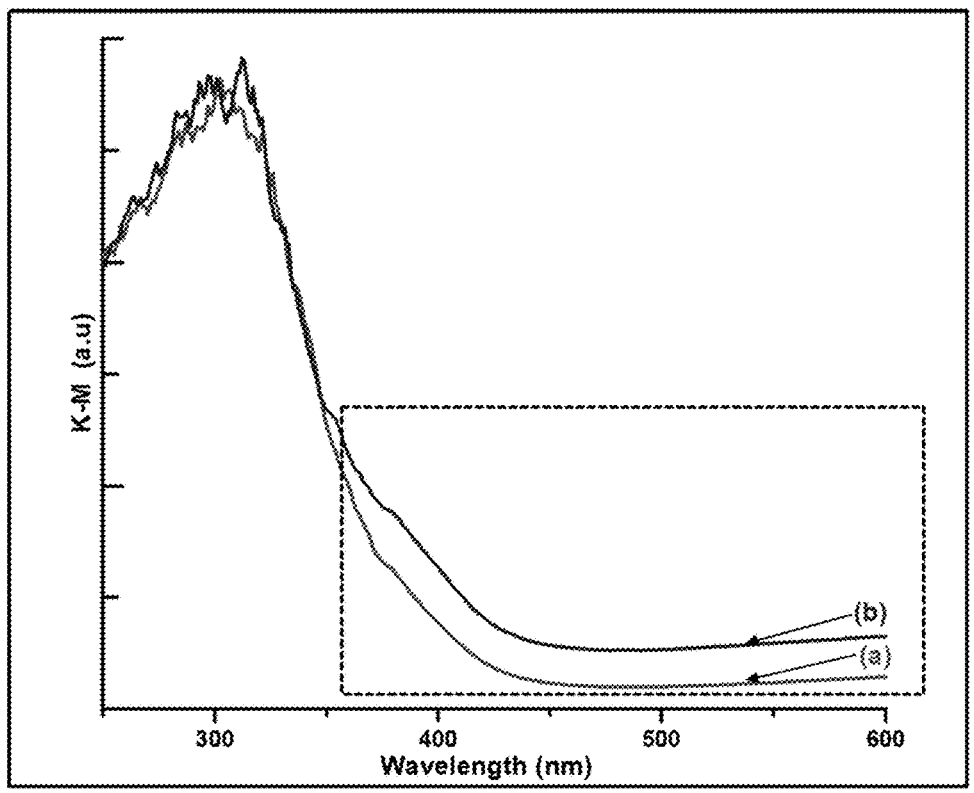
FIG. 5A represents diffuse reflectance spectra according to the Kubelka-Munk function of (a) the non-templated indium-oxide nanoparticles ($In_2O_3$—N), and (b) the templated indium-oxide nanoparticles ($In_2O_3$-T).
Figure 5B:
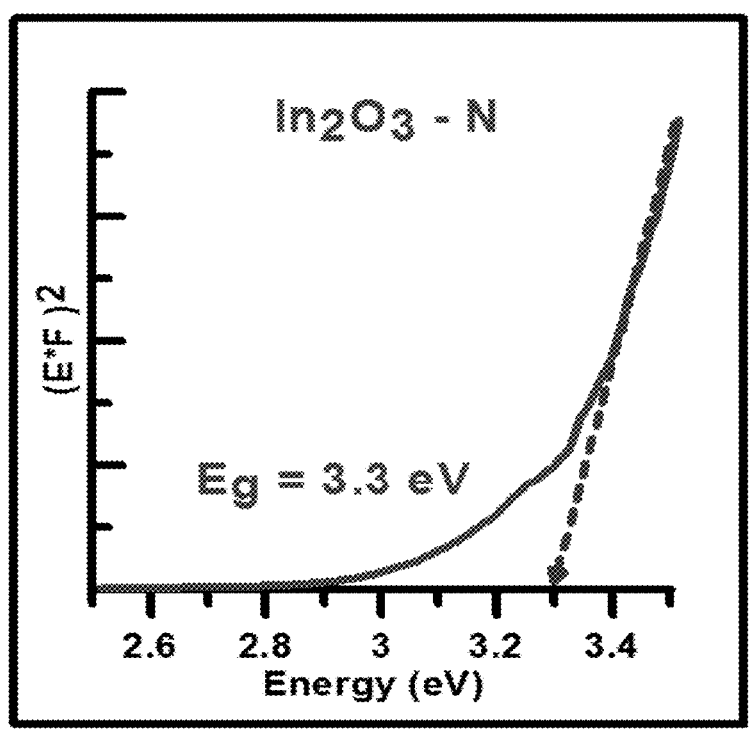
FIG. 5B represents a Tauc plot of the non-templated indium-oxide nanoparticles ($In_2O_3$—N).
Figure 5C:
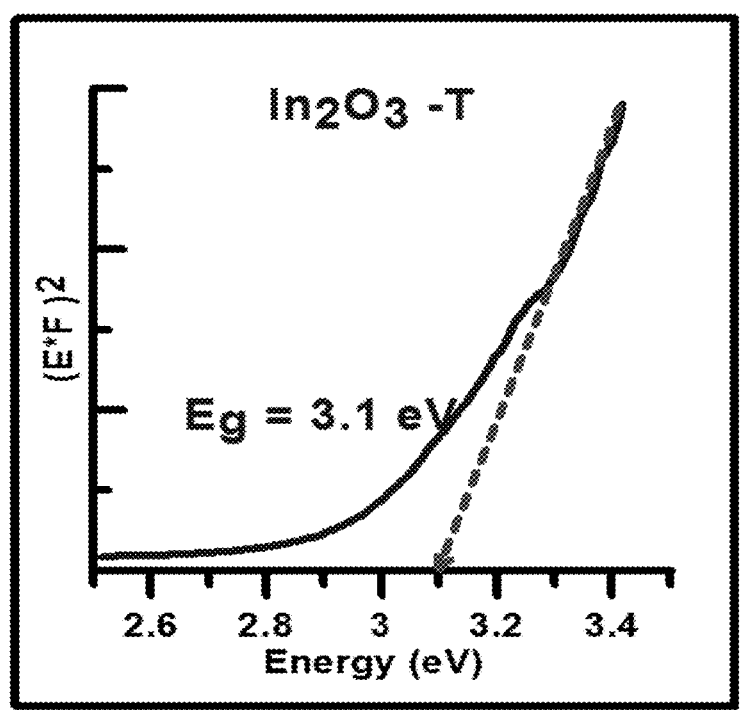
FIG. 5C represents a Tauc plot of the templated indium-oxide nanoparticles ($In_2O_3$-T).

In order to find the band-gap energy ($E_g$) of the semiconducting material, the reflectance spectrum was carried out and was transformed into Kubelka-Munk function [P. Kubelka, F. Munk, Z. *Tech. Phys.* (Leipzig) 12, 593 (1931); P. Kubelka, *J. Opt. Soc. Am.*, 38, 448 (1948)] which is expressed as $F(R)=(I-R)^2/2R=K/S$, where R is the reflectance, K apparent absorption coefficient and S apparent Scattering coefficient. It is clear from the expression of Kubelka-Munk function that it is directly related to the absorbance and hence this function can very well be used in the Tauc plot [J. Tauc, *Mater. Res. Bull.* 3, 37 (1968)] in the place of absorbance to find the band gap energy of the material. For a direct band gap material, $F(R)$ is proportional to $(E-E_g)^{1/2}/E$, where E is the photon energy and $E_g$ is the band gap energy [M. A. Gondal, T. F. Qahatan, M. A. Dastageer, Z. H. Yamani, D. H. Anjum (2015), *J. Nanosci. Nanotech.*, 15, 1 (2015); M. A. Gondal, T. F. Qahtan and M. A. Dastageer, *J. Nanosci. Nanotech.*, 13, 5759 (2013); T. A. Saleh, M. A. Gondal, Q. A. Drmosh, (2012), *Science of Advanced Materials*, 4, 507 (2012)]. FIG. 5A shows the absorption spectra in terms of Kubelka Munk function for $In_2O_3$—N and $In_2O_3$-T, where it is quite obvious that the absorption in the visible region is more for $In_2O_3$-T than $In_2O_3$—N (shown in the dashed box). In addition, FIGS. 5B and 5C show the Tauc plots of $In_2O_3$—N and $In_2O_3$-T from which the band-gap energies for $In_2O_3$—N and $In_2O_3$-T were estimated to be ~3.3 and ~3.1 eV, respectively.

Example 7—Photoluminescence Spectra of $In_2O_3$

Figure 6:
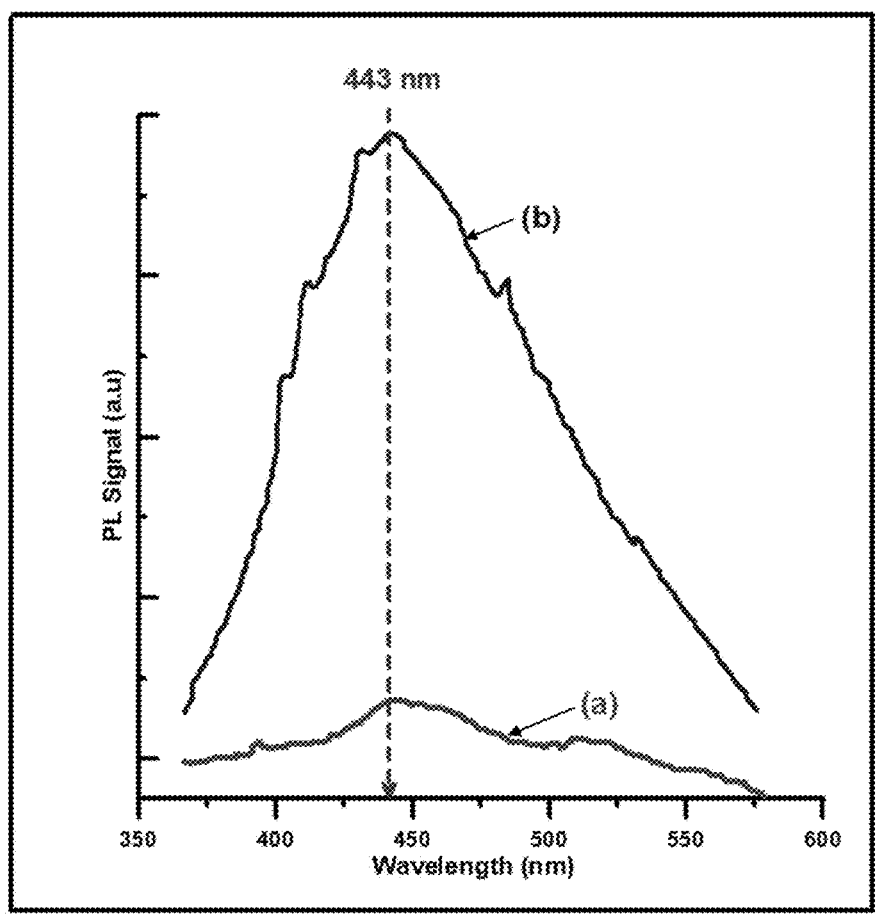
FIG. 6 represents room-temperature photoluminescence spectra of (a) the non-templated indium-oxide nanoparticles ($In_2O_3$—N), and (b) the templated indium-oxide nanoparticles ($In_2O_3$-T).

FIG. 6 depicts the room temperature photoluminescence spectra for the as-prepared mesoporous $In_2O_3$-T and $In_2O_3$—N nanostructures with 350 nm excitation wavelengths, where it was observed that for both the materials, the PL peaks are centered around the wavelength of 443 nm and the PL emission intensity of $In_2O_3$-T is much higher than that of $In_2O_3$—N. In general, emissions can be divided into the near band-edge (NBE) and deep-level (DL) emissions, while the NBE emissions are due to the high crystal quality and quantum confinement effect, while the DL emissions can be favored by low crystallinity or structural defects [H. Yang, L. Liu, H. Liang, J. Wei, Y. Yang. *CrystEngComm.* 13, 5011 (2011)]. The most common radiative processes that lead up to the photoluminescence signal are, electron-hole recombination, band to band recombination, charge carriers binding to the donors, free electron binding to the acceptors and donor acceptor recombination. In the case of mesoporous $In_2O_3$-T, the defect centers induced due to the presence of SBA-15 template luminance through the electron phonon coupling resulting in more prominent PL emission. Also the enhanced photo catalytic activity of $In_2O_3$-T observed in this work indicates that the electron-hole recombination could not be responsible for PL emission from $In_2O_3$-T.

Example 8—Photo-Reduction of $CO_2$ into Methanol

Figure 7A:
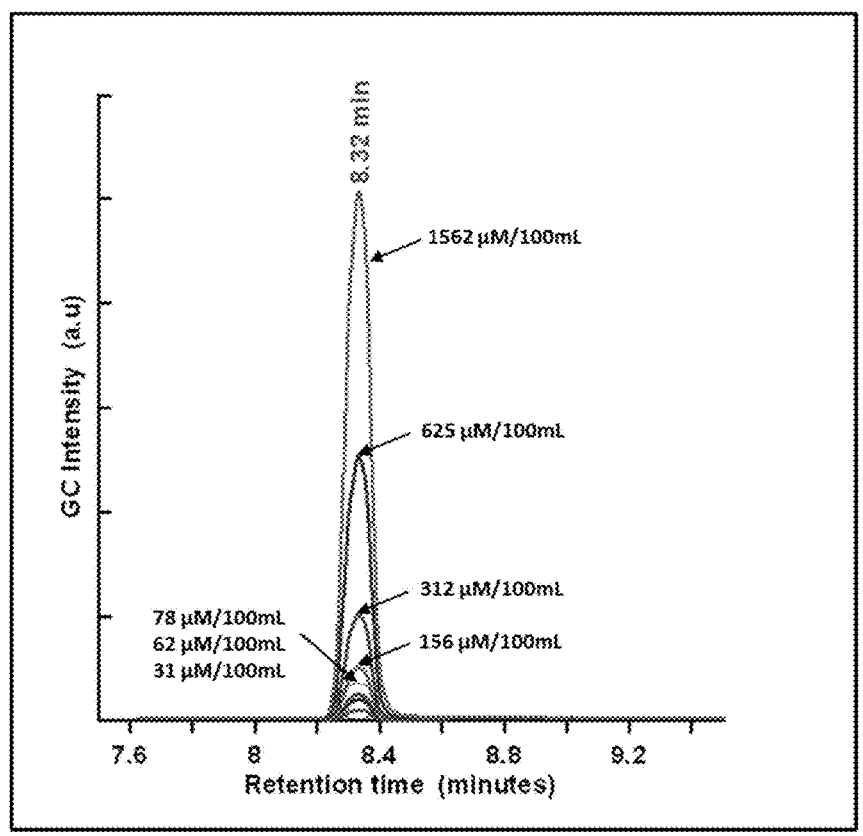
FIG. 7A represents GC chromatograms of standard methanol samples at different methanol concentrations.
Figure 7B:
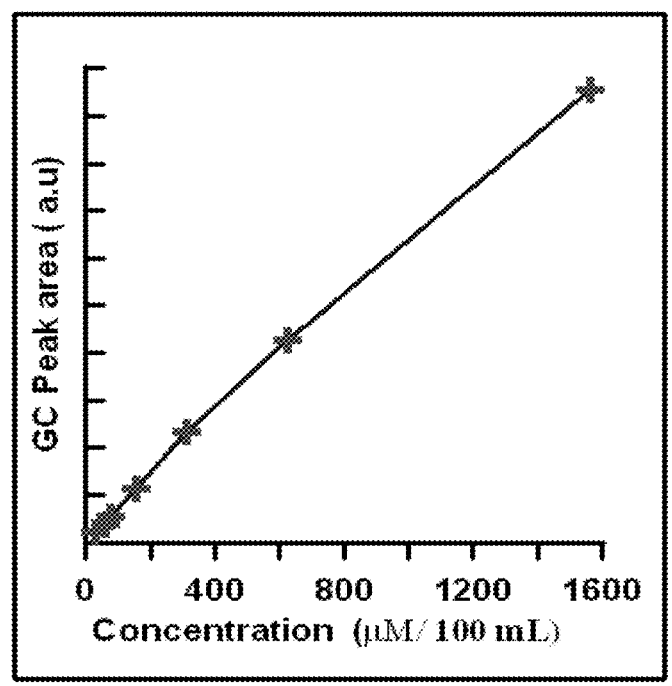
FIG. 7B represents a calibration plot of methanol concentration versus GC peak area.

In order to quantify the methanol produced in our reaction chamber in the chemical process of $CO_2$ reduction, a calibration curve was obtained to correlate the concentration of methanol to the GC peak area at the retention time of 8.32 minutes. Since the retention time for any sample in the gas chromatogram depends on various GC parameters and the nature of GC column, and under our experimental conditions, the observed retention time for methanol standards of different concentrations is 8.32 minutes. Methanol calibration standards of different concentrations were very carefully prepared from the stock solution and the gas chromatograms were recorded for each concentration. Also in order to deplete the traces of methanol sample of one concentration from the GC column, a couple of blank GC runs were carried out prior to injecting the methanol sample of another concentration. FIG. 7A shows a set of chromatogram for methanol standards of known concentrations (31, 63, 78, 156, 313, 625 and 1563 µmol per 100 mL of water) with the GC peaks centered on the retention time of 8.32 minutes and the peak intensity increase with concentration. In addition, FIG. 7B is the linear calibration plot depicting the GC peak area versus methanol concentration, from which the concentrations of methanol that is produced in the reaction were estimated.

In the reaction chamber, $CO_2$ is dissolved in 100 ml of water by constant purging and a 300 mg of photo catalyst is mixed in this solution by constant stirring and the chamber pressure is maintained at 45 PSI. In order to rule out the possibility of getting any reaction product from any kind of non-photocatalytic reactions, we subjected the above reactants and catalyst in the chamber to vigorous stirring for 30 minutes in the absence of laser radiation. The GC analysis of the sample taken out of the chamber after 30 minutes did not show the presence of any product out of this reaction, indicating the absence of any kind of non-photocatalytic reaction. When the reactant catalyst mixture in the chamber is irradiated with 266 nm laser radiation, the photocatalytic reaction is initiated and catalyzed in the reaction chamber to give the desired products. The photocatalytic redox reaction mechanism along with the standard reduction potential are described in the following equations and also shown in the schematic in FIG. 8.

$$SC + h\nu \rightarrow e^- + h^+ \quad \text{(iv)}$$

$$2H_2O + 4h^+ \rightarrow O_2 + 4H^+ \quad E°_{redox} = +0.82 \text{ V} \quad \text{(v)}$$

$$CO_2 + 6H^+ + 6e^- \rightarrow CH_3OH + H_2O \quad E°_{redox} = -0.38 \text{ V} \quad \text{(vi)}$$

Figure 9A:
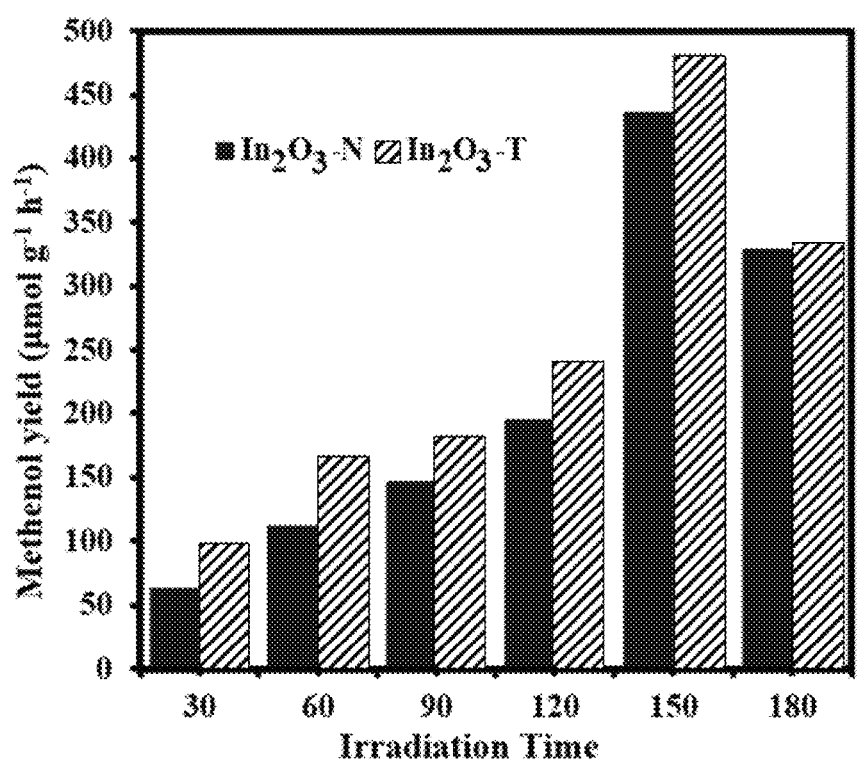
FIG. 9A represents methanol yield versus irradiation time in the presence of the non-templated indium-oxide nanoparticles ($In_2O_3$—N), and the templated indium-oxide nanoparticles ($In_2O_3$-T).

When the light falls on the surface of the photocatalytic material, the electron from the valance band of the semiconductor catalyst goes to the conduction band leaving a hole behind and the generation of this electron-hole pair is vital to initiate and maintain the photocatalytic reaction. It is quite spontaneous that the photo generated charge carriers recombines and releases some form of energy and one of the major requirements to sustain the photocatalytic reaction is the inhibition of this charge recombination. In addition to this, the enhanced light absorption, the reduced particle size, increased surface area, and appropriate band structure are the important factors to be considered in the photocatalyst. The reduced particle size and increased active surface area can enhance the movement of charge carriers to the reactive photo catalytic interface, while the increased absorption and the inhibition of charge recombination facilitates the availability of more charge carriers for sustaining the reaction. As it is clear from the above set of equations, the photo generated electron hole pairs mediate the redox reaction, first generation of $H^+$ through oxidation reaction carried out by holes and then the formation of methanol through reduction reaction carried out by electrons. The least standard reduction potential required by the holes to initiate oxidation of water to create $H^+$ is +0.82 V vs NHE, while the least standard reduction potential required by the electron to carry out $CO_2$ reduction is −0.38 V vs NHE (where NHE refers to normal hydrogen electrode). Hence in order to make this reaction possible, the valence band (VB) edge electrochemical potential of the catalysts must be higher (more positive) than the water splitting reduction potential and at the same time the conduction band (CB) edge should be more negative than the $CO_2/CH_3OH$ reduction potential. In the present work, the locally synthesized non-templated $In_2O_3$—N and mesoporous $In_2O_3$-T nanocrystals were used as a photocatalyst in conjunction with 266 nm laser radiation. As listed in Table 2, the calculated VB and CB edges for $In_2O_3$—N are +2.43 and −0.8 V vs NHE respectively and the same for $In_2O_3$-T are +2.38 and −0.77 V vs NHE respectively. These band structures preliminarily justify the suitability of $In_2O_3$-T and $In_2O_3$—N to initiate and catalyze the photocatalytic reaction to convert the stable $CO_2$ into methanol.

dispensed from the reaction chamber at 30 minute interval for GC analysis and quantification using the calibration curve. The bar charts of FIG. 9A represents the concentrations of methanol produced in the reaction at different irradiation time for both $In_2O_3$-T and $In_2O_3$—N, where it was noticed that for all the irradiation times the concentration of methanol produced with $In_2O_3$-T is consistently higher than that with $In_2O_3$—N. Also, it was observed that the maximum concentration of methanol produced with the $In_2O_3$-T is ~481 $\mu mol g^{-1} h^{-1}$ (at 150 min irradiation time) and the same with $In_2O_3$—N catalyst is ~436 $\mu mol g^{-1} h^{-1}$ (at 150 min irradiation time) under the same experimental conditions. The enhanced photocatalytic activity of mesoporous $In_2O_3$-T nanocrystals can be attributed to the increased specific surface area and the consequent increase of active sites, presence of more lattice defects and the surface roughness as observed in the morphological and XRD studies. According to a recent report [E. Liu, L. Kang, F. Wu, T. Sun, X. Hu, Y. Yang, H. Liu, J. Fan, *Plasmonics* 9, 61 (2014)] the yield of $CO_2$ conversion into methanol using Ag doped $TiO_2$ is 130 $\mu mol g^{-1} h^{-1}$ compared to 130 $\mu mol g^{-1} h^{-1}$ using pure $TiO_2$ as a catalyst and at any rate the methanol yields using both $In_2O_3$-T and $In_2O_3$—N as photocatalyst are better than the yields reported in the literature. FIG. 9A also shows a reduction of methanol yield at 180 minutes of irradiation, which indicates some kind of reverse reaction or the photo-degradation of methanol. These reverse reaction and/or the photo-degradation could be present throughout the process and the predominance of desired $CO_2$ reduction reaction wins over the inhibiting reactions for the first 150 minutes.

Example 9—Quantum Yield of $CO_2$ Conversion into Methanol

The suggested protocol by International Union of Pure and Applied Chemistry (IUPAC) for the quantification of the efficiency of photo conversion is the quantum efficiency or quantum yield Φ, which is defined as [S. Nick, S. Angela, *Pure & Appl. Chem.*, 71, 303 (1999)]

$$\Phi = \frac{\text{ammount (mole) of the product formed}}{\text{ammount of photons (einstein) used}}$$

Figure 9B:
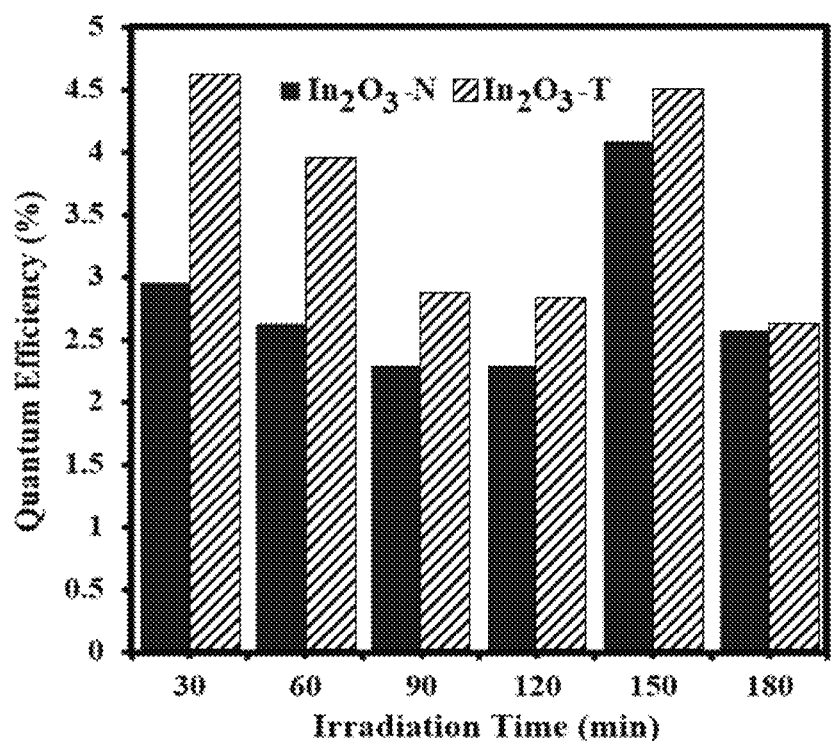
FIG. 9B represents quantum efficiency versus irradiation time in the presence of the non-templated indium-oxide nanoparticles ($In_2O_3$—N), and the templated indium-oxide nanoparticles ($In_2O_3$-T).

We have the amount of methanol molecule in micromoles produced at different irradiation times and the number of 266 nm photons is $3.212 \times 10^{19}$ photons/minute for the pulse energy of 40 mJ/pulse and the pulse repetition rate of 10 Hz and from these we can find the number of photon for any irradiation time in the units of einstein (one Avogadro number of photon is one einstein) to calculate the quantum efficiency. FIG. 9B represents the quantum efficiency of

TABLE 2

Estimated band gaps, calculated conduction band edges, valence band edges, maximum methanol yield and $CO_2$ conversion fficiency for the two $In_2O_3$ nanostructures

| | Estimated energy gap ($E_g$) (eV) | Conduction band edge (eV vs NHE) | Valence band edge (eV vs NHE) | Maximum methanol yield (μmol/ 100 mL) | Quantum yield (%) | Conversion efficiency (%) |
| --- | --- | --- | --- | --- | --- | --- |
| $In_2O_3$-N | 3.23 | −0.80 | +2.43 | 435.83 | 4.00 | 41.9 |
| $In_2O_3$-T | 3.15 | −0.77 | +2.38 | 481.39 | 4.50 | 46.8 |

The methanol produced in the photocatalytic reduction of $CO_2$ is quantified by GC analysis. As the photocatalytic reaction proceeds, 10 micro liters of filtered samples was photocatalytic conversion of $CO_2$ into methanol using $In_2O_3$-T and $In_2O_3$—N. From FIG. 9B it is clear that the quantum yield for mesoporous $In_2O_3$-T is consistently higher than that for the $In_2O_3$—N for all irradiation times considered in this work. The highest quantum yield for $In_2O_3$-T is 4.5% as compared to 4.0% for $In_2O_3$—N, which is approximately 12.5% increase (after 150 minutes of irradiation) brought about by the template version of indium oxide.

Example 10—Conversion Efficiency of $CO_2$ Conversion into Methanol

Figure 9C:
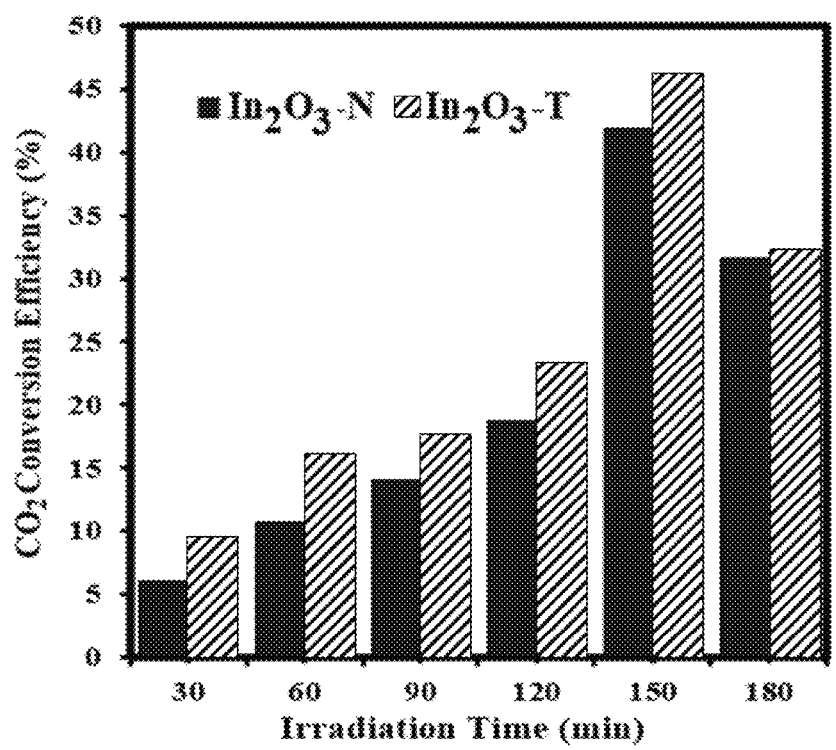
FIG. 9C represents $CO_2$ conversion versus irradiation time in the presence of the non-templated indium-oxide nanoparticles ($In_2O_3$—N), and the templated indium-oxide nanoparticles ($In_2O_3$-T).

In addition, the conversion efficiency of carbon dioxide to methanol was measured, which is defined as the molar ratio of the product and reactant concentrations. According to Henry's law, the amount of $CO_2$ dissolved in 1 L of water at atmospheric pressure is $3.4 \times 10^{-3}$ moles known as Henry's constant. Under our experimental condition, at a pressure of 45 psi, the total $CO_2$ dissolved in 100 mL of water was $1.04 \times 10^{-3}$ moles. FIG. 9C shows the $CO_2$ conversion efficiency with irradiation time where it was observed that the maximum $CO_2$ conversion efficiency achieved is 41.9% for $In_2O_3$—N compared to 46.3% in the case of $In_2O_3$-T, after 150 minutes of irradiation. However, the actual $CO_2$ conversion efficiency may be just lower than the estimated value due to increase in $CO_2$ dissolution rate with increase methanol content in the binary mixture, according to the Schüler's experimental result [N. Schüler, K. Hecht, M. Kraut, R. J. Chem. Eng. Data., 57, 2304 (2012)].

In summary, templated mesoporous indium oxide ($In_2O_3$-T) non-templated indium oxide ($In_2O_3$—N) were used as the photocatalyst to convert $CO_2$ to methanol and the maximum methanol yield observed with $In_2O_3$—N and $In_2O_3$-T were ~436 $\mu mol \cdot g^{-1} h^{-1}$ and ~481 $\mu mol^{-1} h^{-1}$ respectively. The maximum quantum yield with $In_2O_3$-T (after 150 minutes of irradiation) was 4.5% as compared to 4.0% in the case of $In_2O_3$—N. The $CO_2$ conversion efficiency was 46.3% for $In_2O_3$-T and the same for $In_2O_3$—N was about 41.9%.

The invention claimed is:
1. A method of forming methanol, comprising:
thermally decomposing a mixture of $In(NO_3)_3$ hydrate and a template agent to form templated indium-oxide nanoparticles, then
irradiating a mixture comprising water, carbon dioxide, and a photocatalyst with UV light to reduce the carbon dioxide thereby forming methanol,
wherein the photocatalyst comprises the templated indium-oxide nanoparticles having a specific pore volume of 0.08 to 0.15 $cm^3/g$.
2. The method of claim 1, wherein the mixture of the $In(NO_3)_3$ hydrate and templating agent is thermally decomposed at a temperature of 600° C.
3. The method of claim 1, wherein the irradiating is carried out without added hydrogen gas.
4. The method of claim 1,
wherein the photocatalyst further comprises non-templated indium-oxide nanoparticles, and
wherein a weight ratio of the non-templated indium-oxide nanoparticles to the templated indium-oxide nanoparticles is in the range of 10:1 to 1:10.
5. The method of claim 1, further comprising:
injecting carbon dioxide into the mixture at a pressure in the range of 10 to 80 psi during the irradiating.
6. The method of claim 1, wherein the UV light has a wavelength in the range of 150 to 300 nm.
7. The method of claim 1, wherein the UV light is in a form of a single-frequency laser beam with a wavelength in the range of 150 to 300 nm.
8. The method of claim 4,
wherein a methanol yield is in the range of 400 to 500 $\mu mol \cdot h^{-1}$ per gram of the photocatalyst.
9. The method of claim 4,
wherein a conversion efficiency of carbon dioxide to methanol is in the range of 30 to 45% by mole relative to an amount of carbon dioxide, and
wherein a quantum efficiency of forming methanol is in the range of 1.0 to 4.0% by mole relative to an amount of photons absorbed.

\* \* \* \* \*